US011725193B2

(12) United States Patent
Honda et al.

(10) Patent No.: US 11,725,193 B2
(45) Date of Patent: Aug. 15, 2023

(54) MODIFIED GLUCOSE DEHYDROGENASE

(71) Applicant: IKEDA FOOD RESEARCH CO., LTD., Hiroshima (JP)

(72) Inventors: Michinari Honda, Hiroshima (JP); Hirokazu Sanada, Hiroshima (JP); Ryo Takenaka, Hiroshima (JP); Takafumi Takumi, Hiroshima (JP); Takahiro Fujii, Hiroshima (JP)

(73) Assignee: IKEDA FOOD RESEARCH CO., LTD., Hiroshima (JP)

( * ) Notice: Subject to any disclaimer, the term of this patent is extended or adjusted under 35 U.S.C. 154(b) by 706 days.

(21) Appl. No.: 16/619,637

(22) PCT Filed: May 25, 2018

(86) PCT No.: PCT/JP2018/020118
§ 371 (c)(1),
(2) Date: Apr. 9, 2020

(87) PCT Pub. No.: WO2018/230304
PCT Pub. Date: Dec. 20, 2018

(65) Prior Publication Data
US 2022/0098557 A1 Mar. 31, 2022

(30) Foreign Application Priority Data

Jun. 14, 2017 (JP) .................. 2017-116585

(51) Int. Cl.
C12N 9/04 (2006.01)
C12N 15/70 (2006.01)
C12Q 1/32 (2006.01)

(52) U.S. Cl.
CPC ........... C12N 9/0006 (2013.01); C12N 15/70 (2013.01); C12Q 1/32 (2013.01)

(58) Field of Classification Search
CPC ...... C12N 9/0006; C12N 15/70; C12N 15/80; C12N 5/10; C12Q 1/32; C12Q 1/54; C40B 40/08
See application file for complete search history.

(56) References Cited

U.S. PATENT DOCUMENTS 8,445,221 B2   5/2013   Honda et al.
8,969,060 B2   3/2015   Honda et al.
(Continued)

FOREIGN PATENT DOCUMENTS

JP   2015-84676   5/2015
JP   5896375      3/2016
(Continued)

OTHER PUBLICATIONS

Bankar, Sandip B., et al. "Glucose oxidase—an overview." Biotechnology advances 27.4 (2009): 489-501. (Year: 2009).*
(Continued)

Primary Examiner — Louise W Humphrey
Assistant Examiner — Candice Lee Swift
(74) Attorney, Agent, or Firm — Wenderoth, Lind & Ponack, L.L.P.

(57) ABSTRACT

[Problem]
To provide a glucose dehydrogenase with high thermal stability to be used in blood sugar measurement.
[Solution to Problem to problem]
A modified glucose dehydrogenase with an excellent property of high thermal stability that can be obtained by modifying some of amino acids constituting a protein such as a wild-type glucose dehydrogenase, a polynucleotide encoding the enzyme, a method for manufacturing the enzyme, a method for measuring glucose using the enzyme, a measuring reagent composition and a biosen-
(Continued)

sor, and methods for manufacturing the measuring reagent composition and the biosensor.

20 Claims, 1 Drawing Sheet

Specification includes a Sequence Listing.

(56) References Cited

U.S. PATENT DOCUMENTS

| | | | |
|---|---|---|---|
| 2012/0171708 A1 | 7/2012 | Kawaminami et al. | |
| 2013/0168263 A1 | 7/2013 | Sode et al. | |
| 2015/0111280 A1* | 4/2015 | Sumida | C12Y 101/9901 |
| | | | 435/190 |
| 2016/0319246 A1 | 11/2016 | Araki | |

FOREIGN PATENT DOCUMENTS

| | | |
|---|---|---|
| JP | 2016-158578 | 9/2016 |
| WO | 2004/058958 | 7/2004 |
| WO | 2006/101239 | 9/2006 |
| WO | 2008/001903 | 1/2008 |
| WO | 2009/084616 | 7/2009 |
| WO | 2011/034108 | 3/2011 |
| WO | 2012/001976 | 1/2012 |
| WO | 2014/002973 | 4/2014 |
| WO | 2015/099112 | 7/2015 |
| WO | 2017/122650 | 7/2017 |

OTHER PUBLICATIONS

Genbank accession AER13599.1, https://www.ncbi.nlm.nih.gov/protein/353731263/, accessed Sep. 21, 2022 (Year: 2011).*

International Search Report (ISR) dated Aug. 7, 2018 in International (PCT) Application No. PCT/JP2018/020118.

GenBank [online], Accession No. ELA35154, <https://www.ncbi.nlm.nih.gov/protein/ELA35154.1>, Mar. 19, 2015 uploaded, [retrieved on Jul. 9, 2018], Definition: glucose oxidase [Colletotrichum gloeosporioides Nara gc5], cited in CA.

GenBank [online], Accession No. EQB49241, <https://www.ncbi.nlm.nih.gov/protein/eqb49241>, Aug. 13, 2013 uploaded, [retrieved on Jul. 9, 2018], Definition: GMC oxidoreductase [Colletotrichum gloeosporioides Cg-14], cited in CA.

GenBank [online], Accession No. OLN92030, <https://www.ncbi.nlm.nih.gov/protein/oln92030>, Jan. 5, 2017 uploaded, [retrieved on Jul. 9, 2018], Definition: Glucose oxidase 2 [Colletotrichum chlorophyti], cited in CA.

GenBank [online], Accession No. ENH86444, <https://www.ncbi.nlm.nih.gov/protein/enh86444>, Apr. 15, 2015 uploaded, [retrieved on Jul. 9, 2018], Definition: glucose oxidase [Colletotrichum orbiculare MAFF 240422], cited in CA.

GenBank [online], Accession No. EOD53168, <https://www.ncbi.nlm.nih.gov/protein/eod53168>, Mar. 21, 2015 uploaded, [retrieved on Jul. 9, 2018], Definition: putative glucose oxidase protein [Neofusicoccum parvum UCRNP2], cited in CA.

* cited by examiner

```
SEQ_ID_NO:2   1   MLRSIVSLPLLAATALAYPAASSQRFDYVIIGGGTSGLVVANRLSELNNVTVAVIEAGDS   60
SEQ_ID_NO:3   1   ------------------------SSQRFDYVIIGGGTSGLVVANRLSELNNVTVAVIEAGDS   39
SEQ_ID_NO:24  1   MLRSIVSLPLLAATALAYPAASSQRFDYVIIGGGTSGLVVANRLSELNNVTVAVIEAGDS   60
SEQ_ID_NO:25  1   MLRSIVSLPLLAATALAYPAASSQRFDYVIIGGGTSGLVVANRLSELNNVTVAVIEAGDS   60
SEQ_ID_NO:26  1   MRSPLLSLPLFAATALAYPAASSQRFDYVIIGGGTSGLVVANRLSELNNVTVAVIEAGGS   60
SEQ_ID_NO:27  1   MMRSLISLPLFAAAALSYPTASNDRFDYVIVGGGTSGLVVANRLSELNNVTVAVIEAGGS   60
SEQ_ID_NO:28  1   MYSVLATAPLLAATALAAPAA-PAKYDYIVVGGGTSGLVVANRLSELNNVTVAVIEAGGS   59
                                       :.**::.:******.:**********,*

S71 G72
SEQ_ID_NO:2   61  VYDNDNVTSPSKYGLAFGTDIDYAYQTTAQKYGGNKTQTLRAGKALGGTSTINGMAYTSA   120
SEQ_ID_NO:3   40  VYDNDNVTSPSKYGLAFGTDIDYAYQTTAQKYGGNKTQTLRAGKALGGTSTINGMAYTRA   99
SEQ_ID_NO:24  61  VYDNVNVTSPSKYGLAFGTDIDYAYQTTAQKYGGNKTQTLRAGKALGGTSTINGMAYTRA   120
SEQ_ID_NO:25  61  VYDNVNVTSPSKYGLAFGTDIDYAYQTTAQKYGGNKTQTLRAGKALGGTSTINGMAYTRA   120
SEQ_ID_NO:26  61  VFNNANYTDLGSYGKAFGSSIDYAFPTVGQKYGNNETQTLRAGKALGGTSTINGMAYTRA   120
SEQ_ID_NO:27  61  VYDNANYTDLGSYGKAFDTSIDYAYETVGQKYGGNETQTLRAGKALGGTSTINGMAYTRA   120
SEQ_ID_NO:28  60  VFTNENVTNESLYGLAFGTPIDWAYESVNQTYGGGKTQTLRAGKALGGTSTINGMAYTSA   119
                  *:.* ***.   .** **..:**.   .:**:**.*.***********:*********

SEQ_ID_NO:2   121 QDVQIDIWERLGNDGWNWNDLLRYYKRSETLQPPTTVQVDDGVTYIPEDRGTSGPLRVGW   180
SEQ_ID_NO:3   100 QDVQIDIWERLGNDGWNWNDLLKYYKRSETLQPPTTVQVDDGVTYIPELRGTSGPLRVGW   159
SEQ_ID_NO:24  121 QDVQIDIWERLGNDGWNWNDLLKYYKRSETLQAPTTVQVDDGVTYIPEDRGTSGPLRVGW   180
SEQ_ID_NO:25  121 QDVQIDIWERLGNDGWNWNDLLKYYKRSETLQPPTVVQADDGVTYIPEDRGTSGPLRVGW   180
SEQ_ID_NO:26  121 QDVQIDIWERLGNDGWNWENLLEYYKKAETLQPPTTEQVADGVTFTPKDRGSGPLRVGW   180
SEQ_ID_NO:27  121 QSAQVDIWEKLGNDGWNDLLRYYKRSETLERPTARQAARGATIPEDRGTSGPLRVGW   180
SEQ_ID_NO:28  120 EDAQVDAWEAIGNTGWNWASLLPYYKRSERVQPPRAIQLAGGATYDEARGTSGPLRVGW   179
                     *::**.*. ** .**   :* .***:::. ..      .. . .*:.*:*******

G183 S188               G210    A221
SEQ_ID_NO:2   181 KSSGVERKFVDVLNQTYNAVGVPALEDIAGGDMVGWNIYPRTLDTALQVRDAARAYYFP   240
SEQ_ID_NO:3   160 KSSGVERKFVDVLNQTYNAVGVPALEDIAGGDMVGWNIYPRTLDTALQVRDAARAYYFP   219
SEQ_ID_NO:24  181 KSSGVERKFVDVLNQTYNAVGVPALEDIAGGDMVGWNIYPRTLDTALQVRDAARAYYFP   240
SEQ_ID_NO:25  181 KSSGVERKFVDVLNQTYNAVGVPALEDIAGGDMVGWNIYPRTLDTALQVRDAARAYYFP   240
SEQ_ID_NO:26  181 KPQMVNSLFVDVLNQTYNAVGVPALQDIAGGDMVGWNIYPATVDFALQVRDEAARAYYFP   240
SEQ_ID_NO:27  181 KPKMVERLFVDVLNQTYSSVGVPALQDIAGGDMVGWNIYPTVDFTLQVREAARAYYFP   240
SEQ_ID_NO:28  180 KNGMSNIGFPEDLNQTYAANGVPYIYDIAGGRMAGWNVFPQTLDVDLNVREDAARAYYFP   239
                  *  :  : * ::****  .:***    :**** *.***::*   ::. *: ********

S269
SEQ_ID_NO:2   241 YQNRTNFRVFLNTEAQRLVWAEGA---EATASGVLVRDKTGATHTVYANKEVILSAGSLR   297
SEQ_ID_NO:3   220 YQNRTNFRVFLNTEAQRLVWAEGA---EATASGVLVRDKTGATHTVYANKEVILSAGSLR   276
SEQ_ID_NO:24  241 YQNRTNFRVFLNTEAQRLVWAEGA---EATASGVLVRDKSGATRTVYANKEVILSAGSLR   297
SEQ_ID_NO:25  241 YQNRTNFRVFLNTEAQRLVWAEGA---EATASGVLVRDKSGATRTVYANKEVILSAGSLR   297
SEQ_ID_NO:26  241 YQNRTNLRVFLNTEAQKLVWANST---EATASGVLVRDSTGASKTIYANKEVILSAGSLR   297
SEQ_ID_NO:27  241 YQNRTNIRVFLNTEAQKLVWNSSSTANATASGVLVRDATGAVRTHANKEVILSAGSLR   300
SEQ_ID_NO:28  240 FENRTNYRVHLNTEAQKLVWAKSG---AKATASGVLVRDASGNTRKTIYANKEVILSAGSLK   297
                  :.****  * *****:*** .     :*********.:* ::  ::**:*******;

N346
SEQ_ID_NO:2   298 SPLLLEQSGVGNPEILKAAGIQTKLNLPTVGENLQDQMNNGLAQTESSKNFTGVTTFVAYP   357
SEQ_ID_NO:3   277 SPLLLEQSGVGNPEILKAAGIQTKLNLPTVGENLQDQMNNGLAQTESSKNFTGVTTFVAYP   336
SEQ_ID_NO:24  298 SPLLLEQSGVGNPEILKAAGIQTRVNLPTVGENLQDQMNNGLAQTESSKNFTGVTTFVAYP   357
SEQ_ID_NO:25  298 SPLLLEQSGVGNPEILKAAGIQTRVNLPTVGENLQDQMNNGLAQTESSKNFTGVTTFVAYP   357
SEQ_ID_NO:26  298 SPLLLEQSGVGNPEIMKAAGIQTRVNLPIVGENLQDQMNSGLAQSESSKNFTGVTTFVAYP   357
SEQ_ID_NO:27  301 SPLLLEQSGVGNPSIIKAAGIDPKVVLPTVGENLQDQMNNGLAQTESSKNFTGATTFVAYP   360
SEQ_ID_NO:28  298 SPVILELSGVGNADIIKAAGVEVKVDLPAVGERNLQDQTNSGFKGVATRKNFTGNAVNVAYP   357
                  **::**:****. *::****:: ::.**:**.*:***** *:*  ... ::*** :.****

SEQ_ID_NO:2   358 NVDDVFANQTASLAANIKTQLSQWAQDVSETTKGVVTREQLNKFFDIQYDLIFTDKVPLA   417
SEQ_ID_NO:3   337 NVDDVFANQTASLAANIKTQLSQWAQVSEYPNGVVTREQLNKFFDIQYDLIFTDKVPLA   396
SEQ_ID_NO:24  358 NVDDVFANQTASLAANIKTQLSQWAAQVSEYPNGVVTREQLDRFFDIQYDLIFTDKVPLA   417
SEQ_ID_NO:25  358 NVDDVFANQTASLAANIKTQLSQWAAQVSEYPNGVVTREQLDRFFDIQYDLIFTDKVPLA   417
SEQ_ID_NO:26  358 NVDDVFADRTAALAADVYKKSLSQWAAQVSEYPNGVVTREQLRKLAAFFDMQYDLIFTSEVPLA   417
SEQ_ID_NO:27  361 NVDDVFAEQRSPNARVYKRNAQRVSEYPNGAVTREQLAAFFDMQYDLIFTSEVPLA   420
SEQ_ID_NO:28  358 NVEDIFGNRTLIVAADYEKSLQKYAEEASAYSNGVVAVDGLTKFFDIQYDLIFRDKVPLA   417
                  **.*:*.:: ..::..::   ..*  .*:.:*   ...:.  ****:*::******

S427 S429
SEQ_ID_NO:2   418 EILITPAGSRYTEYWALLPFARGNINVTGANGSSAAKINPRYFYMDWDMTEQIGSTAKFIR   477
SEQ_ID_NO:3   397 EILITPAGSRYTEYWALLPFARGNINVTGANGSSAAKINPRYFYMDWDMTEQIGSTAKFIR   456
SEQ_ID_NO:24  418 EILITPAGSRYTEYWALLPFARGNINVTGANGSSAAKINPRYFYMDWDMTEQIGSTAKFIR   477
SEQ_ID_NO:25  418 EILITPAGSRYTEYWALLPFARGNINVTGANGSSTAKINPRYFYMDWDMTEQIGSTAKFIR   477
SEQ_ID_NO:26  418 EILITPAGSRYTEYWALLPFARGNINVYGARNSSPKINPRYFYMDWDMTEQIGSTAKFIR   477
SEQ_ID_NO:27  421 EILVTPAAGSKYTEYWALLPFARGNINVRHAGSSAARIDPRYFYMKWDMTEQVGTAKFIR   480
SEQ_ID_NO:28  418 EVLIYPTDSKAEFWSALLPFARGNVHIASAKADAASAKINPRYFYMPMDWDMTEQIGSTAKYIR   477
                  *:*: *   :  *: ****;**:* *:.: :: *:*:****;*: **  *;**:**;***

F521
SEQ_ID_NO:2   478 QLYKTAPLSQYFASETKPGLATIAEDASDVWSKWILENYRSNFHPVGTTAMMSKELGGV   537
SEQ_ID_NO:3   457 QLYKTAPLSQYFASETKPGLATIAEDASDVWSKWILENYRSNFHPVGTTAMMSKELGGV   516
SEQ_ID_NO:24  478 QLYKTAPLSQYFASETKPGLATIAEDASDDVWSKWILENYRSNFHPVGTTAMMSKELGGV   537
SEQ_ID_NO:25  478 QLYKTAPLSQYFASETKPGLATIAEDASDDVWSKWILENYRSNFHPVGTTAMMSKELGGV   537
SEQ_ID_NO:26  478 QLYKTAPLSQYFANSETKPGLATIAEDASDDVWSKWVIENYRSNFHPVGTTAMMSRELGGV   537
SEQ_ID_NO:27  481 RLYDTAPLSEYFAGETKPGLDVVAEDASDDVWSKWITENYRSNFHPVGTTAMMSRELGGV   540
SEQ_ID_NO:28  478 QLFGTAPLSTYLIANETSPGAAV------ASDAQFESWILENYRSNFHPVGTTAMMSPKELGGV   533
                   *;. *****. *: .::      .:**.  * *.:************;*:*****

V567
SEQ_ID_NO:2   538 VDANLKVYGTSNVRVVDAGVLPFQVCGHLNSTLYAIAEKASDIIKASA---   585
SEQ_ID_NO:3   517 VDANLKVYGTSNVRVVDAGVLPFQVCGHLNSTLYAIAEKASDIIKASA---   564
SEQ_ID_NO:24  538 VDANLKVYGTSNVRVVDAGVLPFQVCGHLNSTLYAIAEKASDIIKASA---   585
SEQ_ID_NO:25  538 VDANLKVYGTSNVRVVDAGVLPFQVCGHLNSTLYAIAEKASDIIKASA---   585
SEQ_ID_NO:26  538 VDANLKVYGTTNVRVVDAGILPFQVCGHLNSTLYAIAEKASDIIKASAWE   587
SEQ_ID_NO:27  541 VDPSLKVYGTSNVRVVDAGVLPFQVCGHLNSTLYAVAEKASDIIKAEA---   588
SEQ_ID_NO:28  534 VDPSLKVYGTSNVRVVDAGVLPFQVCGHLNSTLYAVAEKASDIIKASA---   581
                  **. :*****;*********;**************;*********:*
```

MODIFIED GLUCOSE DEHYDROGENASE

TECHNICAL FIELD

The present invention relates to a glucose dehydrogenase, a polynucleotide encoding the enzyme, a method for manufacturing the enzyme, a method for measuring glucose using the enzyme, a measuring reagent composition, a biosensor and the like.

BACKGROUND ART

Measurement of a blood glucose (blood sugar) concentration is important primarily in blood sugar control for a diabetes patient. For measuring blood sugar, biosensors are widely used as blood sugar meters utilizing enzymes.

As enzymes usable for biosensors, glucose oxidases and glucose dehydrogenases are known. However, the glucose oxidases had problems that measurement errors are caused by dissolved oxygen in the blood. Among the glucose dehydrogenases, flavin-conjugated glucose dehydrogenases derived from eukaryotic cells are not affected by dissolved oxygen, require no addition of coenzymes, and have an excellent substrate specificity, and thus they are useful as enzymes for biosensors (Patent Documents 1 to 5).

PRIOR ART DOCUMENTS

Patent Documents

Patent Document 1: International Publication No. WO 2004/058958
Patent Document 2: International Publication No. WO 2006/101239
Patent Document 3: International Publication No. WO 2008/001903
Patent Document 4: International. Publication No. WO 2009/084616
Patent Document 5: U.S. Pat. No. 5,896,375

SUMMARY OF INVENTION

Problem to be Solved

In blood sugar measurement, an enzyme with higher thermal stability has been desired. The present invention provides a glucose dehydrogenase with high thermal stability, a polynucleotide encoding the enzyme, a method for manufacturing the enzyme, a method for measuring glucose using the enzyme, a measuring reagent composition and a biosensor. Furthermore, the present invention provides methods for manufacturing the measuring reagent composition and the biosensor.

Solution to Problem

The inventors found that a modified glucose dehydrogenase with an excellent property of high thermal stability can be obtained by modifying some of amino acids constituting a protein such as a wild-type glucose dehydrogenase. Furthermore, the inventors found that such an enzyme can be efficiently manufactured using a polynucleotide encoding the enzyme, and that glucose can be measured using the enzyme, to complete the present invention.

That is, the present invention relates to the following aspects.

[Aspect 1]

A modified glucose dehydrogenase consisting of an amino acid sequence containing an amino acid substitution of at least one of amino acids at position corresponding to S71, G72, Q169, G183, S188, G210, A221, 5269, N346, 5427, 5429, F521 or V567 of an amino acid sequence represented by SEQ ID NO: 2 in any of the following amino acid sequences a) to c):

a) an amino acid sequence represented by SEQ ID NO: 2, 3, 24, 25, 26, 27 or 28;
 b) an amino acid sequence in which one or some amino acids are deleted from, replaced in or added to the amino acid sequence represented by SEQ ID NO: 2, 3, 24, 25, 26, 27 or 28; or
 c) an amino acid sequence which has at least 90% similarity to the amino acid sequence represented by 2, 3, 24, 25, 26, 27 or 28.

[Aspect 2]

The modified glucose dehydrogenase according to Aspect 1 containing an amino acid substitution of at least one of amino acids in which, for any of the amino acid sequences a) to c) according to Aspect 1: an amino acid at a position corresponding to S71 is serine, glycine or asparagine; an amino acid at a position corresponding to G72 is glycin; an amino acid at a position corresponding to Q169 is glutamine, tyrosine or phenylalanine; an amino acid at a position corresponding to G183 is glycine or asparagine; an amino acid at a position corresponding to Si 88 is serine; an amino acid at a position corresponding to G210 is glycine; an amino acid at a position corresponding to A221 is alanine or serine; an amino acid at a position corresponding to S269 is serine; an amino acid at a position corresponding to N346 is asparagine or alanine; an amino acid at a position corresponding to S427 is serine or alanine; an amino acid at a position corresponding to S429 is serine; an amino acid at a position corresponding to F521 is phenylalanine; or an amino acid at a position corresponding to V567 is valine.

[Aspect 3]

The modified glucose dehydrogenase according to Aspect 1 or 2, in which the amino acid substitution of at least one of the amino acids at the position corresponding to S71, G72, Q169, G183, S188, G210, A221, 5269, N346, 5427, 5429, F521 or V567 of the amino acid sequence represented by SEQ ID NO: 2 is: substitution of the amino acid at the position corresponding to S71 with aspartic acid; substitution of the amino acid at the position corresponding to G72 with alanine; substitution of the amino acid at the position corresponding to Q169 with cysteine; substitution of the amino acid at the position corresponding to G183 with lysine; substitution of the amino acid at the position corresponding to S188 with valine; substitution of the amino acid at the position corresponding to G210 with cysteine; substitution of the amino acid at the position corresponding to A221 with tyrosine; substitution of the amino acid at the position corresponding to S269 with valine; substitution of the amino acid at the position corresponding to N346 with lysine; substitution of the amino acid at the position corresponding to S427 with valine; substitution of the amino acid at the position corresponding to S429 with valine; substitution of the amino acid at the position corresponding to F521 with tryptophan or tyrosine; or substitution of the amino acid at the position corresponding to V567 with alanine, cysteine, glycine, methionine, glutamine, scrine or thrconinc.

[Aspect 4]

The modified glucose dehydrogenase according to any one of Aspects 1 to 3, which has, after a treatment in 0.1M phosphate buffer (pH 6.0) at 45° C. for 30 minutes, a residual activity greater than that of a wild-type enzyme.

[Aspect 5]

A polynucleotide encoding the modified glucose dehydrogenase according to any one of Aspects 1 to 4.

[Aspect 6]

A recombinant vector containing the polynucleotide according to Aspect 5.

[Aspect 7]

A transformant cell transformed using the vector according to Aspect 6.

[Aspect 8]

A method for manufacturing a modified glucose dehydrogenase, characterized in that the transformant cell according to Aspect 7 is cultured, and the modified glucose dehydrogenase is collected from a resultant culture.

[Aspect 9]

A method for measuring glucose using the modified glucose dehydrogenase according to any one of Aspects 1 to 4.

[Aspect 10]

A glucose measuring reagent composition containing the modified glucose dehydrogenase according to any one of Aspects 1 to 4.

[Aspect 11]

A biosensor for measuring glucose containing the modified glucose dehydrogenase according to any one of Aspects 1 to 4.

Effects of the Invention

The present invention makes it possible to utilize a modified glucose dehydrogenase with excellent thermal stability. Furthermore, the present invention allows efficient manufacture of the modified glucose dehydrogenase according to the present invention, and more stable manufacture can be achieved even by a biosensor manufacturing process including a heating step.

BRIEF DESCRIPTION OF DRAWINGS

FIG. 1 illustrates an alignment of each sequence.

DESCRIPTION OF EMBODIMENTS

A "modified glucose dehydrogenase" according to the present invention is an enzyme having a glucose dehydrogenase activity (glucose dehydrogenase) in which some of amino acids constituting a wild-type protein such as a glucose dehydrogenase are replaced with other amino acids.

Herein, an amino acid residue may be represented by a single-letter notation. For example, an amino acid substitution in which an amino acid corresponding to serine at a seventy-first amino acid of the amino acid sequence represented by SEQ ID NO: 2 is replaced with aspartic acid is represented as S71D.

The modified glucose dehydrogenase according to the present invention contains an amino acid substitution of at least one of amino acids at position corresponding to S71, G72, Q169, G183, S188, G210, A221, S269, N346, S427, S429, F521 or V567 of an amino acid sequence represented by SEQ ID NO: 2 in the amino acid sequence constituting the wild-type protein.

Examples of an amino acid sequence of a pre-modified (wild-type) glucose dehydrogenase include: an amino acid sequence represented by SEQ ID NO: 2 or 3; or amino acid sequences having homology with the above-mentioned amino acid sequence and a glucose dehydrogenase activity. Note that the amino acid sequence represented by SEQ ID NO: 3 is an amino acid sequence represented by SEQ ID NO: 2 but not containing a signal sequence. Furthermore, examples of the amino acid sequence constituting the wild-type protein include: L2G906 (SEQ ID NO: 24), TOLBU8 (SEQ ID NO: 25), A0A1Q8RY40 (SEQ ID NO: 26), N4VGS5 (SEQ ID NO: 27) and R1EZF7 (SEQ ID NO: 28), which are sequences published by UniProt; or amino acid sequences having homology with the above-mentioned amino acid sequences. Each of the amino acid sequences of SEQ ID NOs: 24 to 28 has 99%, 99%, 98%, 96%, and 92% similarity to SEQ ID NO: 2, respectively.

The modified glucose dehydrogenase according to the present invention is a protein having an amino acid sequence containing an amino acid substitution of at least one of amino acids at position corresponding to S71, G72, Q169, G183, S188, G210, A221, S269, N346, S427, S429, F521 or V567 of an amino acid sequence represented by SEQ ID NO: 2 in:

(a) an amino acid sequence represented by SEQ ID NO: 2, 3, 24, 25, 26, 27 or 28;

(b) an amino acid sequence in which one or some amino acids are deleted from, replaced in or added to the amino acid sequence represented by SEQ ID NO: 2, 3, 24, 25, 26, 27 or 28; or (c) an amino acid sequence which has homology with the amino acid sequence represented by 2, 3, 24, 25, 26, 27 or 28.

The phrase "one or some amino acids are deleted from, replaced in or added to" means deletion, replacement and/or addition of preferably at most 60, more preferably at most 55, 50, 40, 30, 20, 10 or 5 amino acids.

The phrase that an amino acid sequence has "homology" means that similarity of the amino acid sequence is preferably at least 90% or 95%, more preferably at least 96%, 97%, 98% or 99%, or alternatively that identity of the amino acid sequence is preferably at least 60%, 65%, 70%, 75%, 80%, 85%, 90%, 92%, 95%, 98% or 99%.

The similarity is a value calculated as [the number of letters in which a score becomes 0 or more in alignment]/[alignment length] using a score table of Table 1 (Manual of GENETYX (registered trademark), p. 220, A. 18 Homology Score Table, A.18.2, Amino Acids; reference document: Atlas of Protein Sequence and Structure Vol. 5 (1978)). It can be calculated using a sequence analysis software GENETYX ((registered trademark), GENETYX CORPORATION). More specifically, this software is used in its default setting to analyze homology between amino acid sequences and calculate it as the similarity.

The identity is based on a value of identity calculated by the homology analysis between amino acid sequences with GENETYX (registered trademark: GENETYX CORPORATION).

TABLE 1

| | C | S | T | P | A | G | N | D | E | Q | H | R | K | M | I | L | V | F | Y | W | B | Z | X |
|---|---|---|---|---|---|---|---|---|---|---|---|---|---|---|---|---|---|---|---|---|---|---|---|
| C | 12 | 0 | −2 | −3 | −2 | −3 | −4 | −5 | −5 | −5 | −3 | −4 | −5 | −5 | −2 | −6 | −2 | −4 | 0 | −8 | −4 | −5 | 0 |
| S | 0 | 2 | 1 | 1 | 1 | 1 | 1 | 0 | 0 | −1 | −1 | 0 | 0 | −2 | −1 | −3 | −1 | −3 | −3 | −2 | 0 | 0 | 0 |
| T | −2 | 1 | 3 | 0 | 1 | 0 | 0 | 0 | 0 | −1 | −1 | −1 | 0 | −1 | 0 | −2 | 0 | −3 | −3 | −5 | 0 | −1 | 0 |
| P | −3 | 1 | 0 | 6 | 1 | −1 | −1 | −1 | −1 | 0 | 0 | 0 | −1 | −2 | −2 | −3 | −1 | −5 | −5 | −6 | −1 | 0 | 0 |
| A | −2 | 1 | 1 | 1 | 2 | 1 | 0 | 0 | 0 | 0 | −1 | −2 | −1 | −1 | −1 | −2 | 0 | −4 | −3 | −6 | 0 | 0 | 0 |
| G | −3 | 1 | 0 | −1 | 1 | 5 | 0 | 1 | 0 | −1 | −2 | −3 | −2 | −3 | −3 | −4 | −1 | −5 | −5 | −7 | 0 | −1 | 0 |
| N | −4 | 1 | 0 | −1 | 0 | 0 | 2 | 2 | 1 | 1 | 2 | 0 | 1 | −2 | −2 | −3 | −2 | −4 | −2 | −4 | 2 | 1 | 0 |
| D | −5 | 0 | 0 | −1 | 0 | 1 | 2 | 4 | 3 | 2 | 1 | −1 | 0 | −3 | −2 | −4 | −2 | −6 | −4 | −7 | 3 | 3 | 0 |
| E | −5 | 0 | 0 | −1 | 0 | 0 | 1 | 3 | 4 | 2 | 1 | −1 | 0 | −2 | −2 | −3 | −2 | −5 | −4 | −7 | 2 | 3 | 0 |
| Q | −5 | −1 | −1 | 0 | 0 | −1 | 1 | 2 | 2 | 4 | 3 | 1 | 1 | −1 | −2 | −2 | −2 | −5 | −4 | −5 | 1 | 3 | 0 |
| H | −3 | −1 | −1 | 0 | −1 | −2 | 2 | 1 | 1 | 3 | 6 | 2 | 0 | −2 | −2 | −2 | −2 | −2 | 0 | −3 | 1 | 2 | 0 |
| R | −4 | 0 | −1 | 0 | −2 | −3 | 0 | −1 | −1 | 1 | 2 | 6 | 3 | 0 | −2 | −3 | −2 | −4 | −2 | 2 | −1 | 0 | 0 |
| K | −5 | 0 | 0 | −1 | −1 | −2 | 1 | 0 | 0 | 1 | 0 | 3 | 5 | 0 | −2 | −3 | −2 | −5 | −4 | −3 | 1 | 0 | 0 |
| M | −5 | −2 | −1 | −2 | −1 | −3 | −2 | −3 | −2 | −1 | −2 | 0 | 0 | 0 | 2 | 4 | 2 | 0 | −2 | −4 | −2 | −2 | 0 |
| I | −2 | −1 | 0 | −2 | −1 | −3 | −2 | −2 | −2 | −2 | −2 | −2 | −2 | 2 | 5 | 2 | 4 | 1 | −1 | −5 | −2 | −2 | 0 |
| L | −6 | −3 | −2 | −3 | −2 | −4 | −3 | −4 | −3 | −2 | −2 | −3 | −3 | 4 | 2 | 6 | 2 | 2 | −1 | −2 | −3 | −3 | 0 |
| V | −2 | −1 | 0 | −1 | 0 | −1 | −2 | −2 | −2 | −2 | −2 | −2 | −2 | 2 | 4 | 2 | 4 | −1 | −2 | −6 | −2 | −2 | 0 |
| F | −4 | −3 | −3 | −5 | −4 | −5 | −4 | −6 | −5 | −5 | −2 | −4 | −5 | 0 | 1 | 2 | −1 | 9 | 7 | 0 | −5 | −5 | 0 |
| Y | 0 | −3 | −3 | −5 | −3 | −5 | −2 | −4 | −4 | −4 | 0 | −4 | −4 | −2 | −1 | −2 | 7 | 10 | 0 | −3 | −4 | 0 | |
| W | −8 | −2 | −5 | −6 | −6 | −7 | −4 | −7 | −7 | −5 | −3 | 2 | −3 | −4 | −5 | −2 | −6 | 0 | 0 | 17 | −5 | −6 | 0 |
| B | −4 | 0 | 0 | −1 | 0 | 0 | 2 | 3 | 2 | 1 | 1 | −1 | 1 | −2 | −2 | −3 | −2 | −5 | −3 | −5 | 2 | 2 | 0 |
| Z | −5 | 0 | −1 | 0 | 0 | −1 | 1 | 3 | 3 | 3 | 2 | 0 | 0 | −2 | −2 | −3 | −2 | −5 | −4 | −6 | 2 | 3 | 0 |
| X | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

The phrase "position corresponding to S71, G72, Q169, G183, S188, G210, A221, S269, N346, S427, S429, F521 or V567 of an amino acid sequence represented by SEQ ID NO: 2" for the amino acid sequence of the glucose dehydrogenase means the position corresponding to serine at position 71, glycine at position 72, glutamine at position 169, glycine at position 183, serine at position 188, glycine at position 210, alanine at position 221, serine at position 269, asparagine at position 346, serine at position 427, serine at position 429, phenylalanine at position 521, or valine at position 567, provided that a starting amino acid, methionine (M), of the amino acid sequence represented by SEQ ID NO: 2 is at position 1, and the position can be identified by sequence alignment with SEQ ID NO: 2. For example, the corresponding position can be identified as shown in FIG. 1.

The amino acids at the corresponding positions are preferably: serine, glycine or asparagine for S71; glycine for G72; glutamine, tyrosine or phenylalanine for Q169; glycine or asparagine for G183; serine for S188; glycine for G210; alanine or serine for A221; serine for S269; asparagine or alanine for N346; serine or alanine for S427; serine for S429; phenylalanine for F521; and valine for V567.

In addition, the amino acid substitution is preferably: S71D; G72A; Q169C; G183K; S188V; G210C; A221Y; S269V; N346K; S427V; S429V; F521W or F521Y; or V567A, V567C, V567G, V567M, V567Q, V567S or V567T alanine. That is, at least one of the followings preferably occurs: an amino acid at a position corresponding to S71 is replaced with aspartic acid; an amino acid at a position corresponding to G72 is replaced with alanine; an amino acid at a position corresponding to Q169 is replaced with cysteine; an amino acid at a position corresponding to G183 is replaced with lysine; an amino acid at a position corresponding to S188 is replaced with valine; an amino acid at a position corresponding to G210 is replaced with cysteine; an amino acid at a position corresponding to A221 is replaced with tyrosine; an amino acid at a position corresponding to S269 is replaced with valine; an amino acid at a position corresponding to N346 is replaced with lysine; an amino acid at a position corresponding to S427 is replaced with valine; an amino acid at a position corresponding to S429 is replaced with valine; an amino acid at a position corresponding to F521 is replaced with tryptophan or tyrosine; or an amino acid at a position corresponding to V567 is replaced with alanine, cysteine, glycine, methionine, glutamine, serine or threonine.

The modified glucose dehydrogenase of the present invention preferably has a residual activity of the glucose dehydrogenase activity higher than that of the wild-type enzyme. Note that the residual activity of each enzyme should be a ratio of an activity after a treatment in 0.1 M phosphate buffer (pH 6.0) at 45° C. for 30 minutes with respect to an activity before this treatment. The percentage of residual activity of the modified glucose dehydrogenase of the present invention with respect to the residual activity of the wild-type enzyme is preferably 102% or more, more preferably 110% or more, still more preferably 120% or more, and most preferably 130% or more.

The polynucleotide of the present invention is a polynucleotide encoding the modified glucose dehydrogenase according to any one of Aspects 1 to 4. The polynucleotide may be a sequence containing an intron, or cDNA. Examples of the polynucleotide includes a polynucleotide which is obtained by introducing mutation into a polynucleotide encoding an amino acid sequence represented by SEQ ID NO: 2, 3, 24, 25, 26, 27 or 28, or an amino acid sequence having homology with the above-mentioned amino acid sequence.

The polynucleotide of the present invention can be easily prepared with well-known methods. For example, a polynucleotide encoding an amino acid sequence represented by SEQ ID NO: 2, 3, 24, 25, 26, 27 or 28, or an amino acid sequence having homology with the above-mentioned amino acid sequence is used as a template, and mutation is introduced thereinto by various well-known PCR methods using suitable set of primers so as to prepare the polynucleotide of the present invention. Alternatively, it can be artificially synthesized. It can be a polynucleotide in which codon usage is optimized dependent on a transformant cell.

As the polynucleotide used as the template, the sequence of SEQ ID NO: 1 may be synthesized. Alternatively, a gene sequence can be used as the template, which encodes an amino acid sequence found to have similarity and/or identity in a homology search such as BLAST (blastp or tblastn)

between the amino acid sequence of SEQ ID NO: 2 and the published sequence. It can be obtained by: designing a primer from the published sequence; and amplifying it by PCR or RT-PCR using as a template DNA or RNA of a strain from which the gene sequence is derived. It also can be obtained from strains of the same species or genus as those of the strain from which the published sequence is derived. Alternatively, it can be synthesized according to published sequence information. The similarity is preferably at least 90%, 95%, 96%, 97%, 98%, or 99%. The identity is preferably at least 60%, 65%, 70%, 75%, 80%, 85%, 90%, 92%, 95%, 98%, or 99%. Note that the sequence of SEQ ID NO: 1 is a base sequence encoding the amino acid sequence of SEQ ID NO: 2 which is an amino acid sequence of the wild-type glucose dehydrogenase.

The recombinant vector of the present invention is a cloning vector or an expression vector, and the vector is appropriately selected and contains the polynucleotide of the present invention as an insert. The insert may include an intron when the host is a eukaryotic cell. The expression vector may be any of an expression vector for a prokaryotic cell or an expression vector for a eukaryotic cell. Examples thereof can include a pUC system, pBluescriptII, a pET expression system, a pGEX expression system, pCold expression system and the like, but a vector capable of mass expression of proteins is preferred. Note that if necessary, a polynucleotide that contributes to expression of chaperone, lysozyme and the like can be introduced into the same and/or different vector as the polynucleotide of the present invention.

The transformant cell of the present invention can be obtained by transforming with the vector of the present invention, e.g. prokaryotic cells such as *Escherichia coli* and *Bacillus subtilis*, eukaryotic cells such as Eumycetes (yeast, filamentous fungus (ascomycete, basidiomycete, etc.), insect cell and mammal cell, etc.

A recombinantly modified glucose dehydrogenase according to the present invention can be manufactured by collecting the modified glucose dehydrogenase from a culture obtained by culturing the transformant cell of the present invention.

For culturing microorganisms that produce the modified glucose dehydrogenase used in the present invention, conventional medium for culturing microorganisms can be used. Either a synthesized medium or a natural medium may be used, as long as the medium moderately contains carbon sources, nitrogen sources, vitamins, minerals and other micronutrients required by the microorganisms of use. As the carbon sources, glucose, sucrose, dextrin, starch, glycerol, molasses, etc. can be used. As the nitrogen sources, inorganic salts such as ammonium chloride, ammonium nitrate, ammonium sulfate and ammonium phosphate, amino acids such as DL-alanine and L-glutamic acid, nitrogen-containing natural products such as peptone, meat extract, yeast extract, malt extract and corn steep liquor can be used. As the vitamins, riboflavin, pyridoxine, niacin (nicotinic acid), thiamin, etc. As the minerals, monosodium phosphate, disodium phosphate, monopotassium phosphate, dipotassium phosphate, magnesium sulfate, ferric chloride, etc. can be used.

The culturing for obtaining the modified glucose dehydrogenase of the present invention should be generally carried out under an aerobic condition by a method such as shake culture and aeration agitation. A culture condition suitable for production of the glucose dehydrogenase should be set in consideration of the properties of a glucose dehydrogenase-producing bacterium. For example, the culturing is carried out preferably at a culture temperature of 20° C. to 50° C., in a range of pH 4 to pH 8, and the pH may be adjusted during the culture in consideration of producibility. The culture period is preferably 2 to 10 days. However, the culture time can be extended in the case where feeding or continuous culture is carried out in order to increase an amount of the production. By culturing with such a method, the modified glucose dehydrogenase can be produced and accumulated in a culture.

For the method for obtaining the modified glucose dehydrogenase from a culture, a conventional method for manufacturing proteins can be used. For example, first, a modified glucose dehydrogenase-producing bacterium is cultured, and then a culture supernatant is obtained by centrifugation. Alternatively, the cultured fungus body is obtained, the cultured microorganism is crushed by an appropriate manner, and supernatants are obtained from the crushed liquid by centrifugation or the like. Next, the modified glucose dehydrogenase contained in these supernatants can be purified by a conventional method for purifying proteins to obtain a purified enzyme. For example, the glucose dehydrogenase can be purified by combining purifying manipulations such as ultrafiltration, salt precipitation, solvent precipitation, heat treatment, dialysis, ion-exchange chromatography, hydrophobic chromatography, gel filtration and affinity chromatography.

The modified glucose dehydrogenase of the present invention can be used in a dried state. Although the drying method is not limited as long as the enzyme is not deactivated, it is preferable to obtain a lyophilized product through lyophilization. In the drying process, a buffer solution agent and a stabilizer can be added. It may be crushed and powderized so as to obtain a powdered product.

Glucose can be measured by using the modified glucose dehydrogenase of the present invention. The method for measuring glucose of the present invention can include a step for bringing the test sample containing glucose into contact with the modified glucose dehydrogenase of the present invention, so as to quantify glucose in a test sample. Although the test sample in the present invention is not particularly limited, it can be exemplified by biological samples, specifically blood, tear, saliva, urine or interstitial fluid, etc. The enzyme of the present invention is useful particularly for measuring blood sugar.

The present invention provides a manufacturing method for manufacturing a reagent composition for measuring glucose, a kit for measuring glucose, or a biosensor for measuring glucose using the modified glucose dehydrogenase of the present invention. Since the enzyme of the present has high substrate specificity and does not use oxygen as an electron acceptor, it is hardly affected by other saccharides and dissolved oxygen in the measured sample. Therefore, the reagent composition for measuring glucose, the kit for measuring glucose or the biosensor for measuring glucose which are hardly affected by other saccharides and dissolved oxygen can be provided, allowing the glucose measurement with high measurement accuracy.

The reagent composition for measuring glucose of the present invention may be any reagent composition as long as it contains the glucose dehydrogenase of the present invention as an enzyme. The amount of the enzyme in the composition is not particularly limited as long as the glucose in samples can be measured, but the amount of the enzyme per measurement is preferably about 0.01 to 100 U, more preferably about 0.05 to 50 U, and further preferably about 0.1 to 20 U. The composition preferably contains a buffer, and any other optional components known to those skilled in the art such as a stabilizer are preferably contained to enhance thermal stability and storage stability of the enzyme and reagent components. The composition can be exemplified by a bovine serum albumin (BSA) or egg albumin, a sugar or a sugar alcohol not interactive with the enzyme, a carboxyl group-containing compound, an alkaline earth metal compound, an ammonium salt, sulfate, proteins or the like. Furthermore, a known substance which reduces the influence from impurities affecting the measurement in the test sample may also be be contained in the measuring reagent. The kit for measuring glucose of the present invention contains the above-mentioned reagent composition, and may contain a glucose standard solution.

The biosensor of the present invention may be any sensor as long as it contains the modified glucose dehydrogenase of the present invention as an enzyme. For example, an electrochemical biosensor is made by comprising a substrate, a counter electrode, a working electrode, a mediator and the above-described enzyme. The mediator can be exemplified by a proteinic electronic mediator such as heme, a ferricyanide compound, a quinone compound, an osmium compound, a phenazine compound, a phenothiazine compound, etc. Moreover, a biosensor adapted to detecting ion change, coloring intensity, pH change or the like can also be constituted. Glucose measurement is possible by using this biosensor.

Furthermore, the modified glucose dehydrogenase of the present invention can be used for a bio battery. The bio battery of the present invention is composed of an anode electrode for oxidation reaction and a cathode electrode for reduction reaction, and optionally includes an electrolyte layer which separates between the anode and the cathode as required. An enzyme electrode containing the electron mediators and the glucose dehydrogenase is used for the anode electrode, electrons generated by oxidation of the substrate are collected on the electrode, and protons are generated. Meanwhile, an enzyme to be generally used for the cathode electrode may be used on the cathode side, for example laccase, ascorbate oxidase or bilirubin oxidase is used, and the proton generated on the anode side is reacted with oxygen to generate water. As the electrode, electrodes generally used for the bio battery, such as carbon, gold and platinum group metal can be used.

In measuring the activity of the enzyme of the present invention, the enzyme is optionally diluted to a final concentration of preferably 0.15-0.6 U/mL for use. Note that a unit of enzyme activity of the enzyme (U) means an enzyme activity for oxidizing 1 μmol of glucose in one minute. The enzyme activity of the modified glucose dehydrogenase of the present invention can be measured by the following method.

(Method for Measuring Glucose Dehydrogenase (GLD) Activity)

1.00 mL of 100 mM potassium phosphate buffer (pH 6.0), 1.00 mL of 1 M D-glucose solution, 0.14 mL of 3 mM 2,6-dichlorophenolindophenol (hereinafter called DCIP), and 0.20 mL of 3 mM 1-methoxy-5-methylphenazinium methylsulfate, as well as 0.61 mL of ultrapure water were mixed, kept at 37° C. for 10 minutes, and then 0.05 mL of enzyme solution was added, and the reaction was initiated. For 5 minutes from the initiation of the reaction, a decrement per one minute of the absorbance at 600 nm (ΔA600) associated with progression of the enzyme reaction was measured to calculate the enzyme activity from a straight part according to the following formula. In this measurement, for the enzyme activity, an enzyme amount for reducing 1 μmol of DCIP at 37° C., pH 6.0 per one minute was defined as 1 U.

Glucose dehydrogenase(GLD)activity(U/mL)=(−(ΔA600−ΔA600blank)×3.0×dilution ratio of enzyme)/(10.8×1.0×0.05)

Note that, in the formula, 3.0 represents a liquid volume (mL) of the reaction reagent+the enzyme solution, 10.8 represents a molar absorption coefficient of DCIP at pH 6.0, 1.0 represents an optical path length (cm) of a cell, 0.05 represents a liquid volume (mL) of the enzyme solution, and ΔA600blank represents a decrement of the absorbance at 600 nm per minute in the case that the reaction is initiated by adding a dilute solution of the enzyme instead of the enzyme solution.

Hereinafter, the present invention will be specifically explained by Examples. However, the present invention is not limited by the following Examples. The contents described in the references cited in the present specification have been incorporated into the present specification as a part of its disclosure.

Example 1

(Obtaining the Flavin-Conjugated Wild-Type Glucose Dehydrogenase (GLD))

GLD-producing bacteria were searched. As a result, GLD activity has been confirmed in the culture supernatants of *Glomerella fructigena* NBRC5951.

(1) Culture of Fungus Bodies

A liquid medium consisting of 4% (w/v) of Pinedex (Matsutani Chemical Industry Co., Ltd.), 1% (w/v) of defatted soybean (Showa Sangyo Co., Ltd.), 1% (w/v) of corn steep liquor (San-ei Sucrochemical Co., Ltd.), 0.5% (w/v) of potassium dihydrogenphosphate (NACALAI TESQUE, INC.), 0.05% (w/v) of magnesium sulfate heptahydrate (NACALAI TESQUE, INC.) and water was adjusted to have a pH of 6.0, and 10 mL of the liquid medium was introduced into a big test tube, and autoclaved at 121° C. for 20 minutes. The GLD-producing bacteria were inoculated to the cooled liquid medium, and shake-cultured at 25° C. for 72 hours, and then moist fungus body was collected by means of bleached cloth.

(2) Isolation of the Total RNA

After 200 mg of the moist fungus body obtained in (1) was frozen at −80° C., 100 μg of the total RNA was extracted using ISOGENII (NIPPON GENE CO., LTD.).

(3) Preparation of a cDNA Library

A cDNA library was prepared from the RNA obtained in (2) by a reverse transcription reaction, using a reverse transcriptase and an oligo dT primer with an adaptor sequence. "SMARTer RACE cDNA Amplification kit" (TAKARA BIO INC.) was used as a reaction reagent, and the reaction condition was adopted to a protocol described in an operating manual.

(4) Cloning of GLD Gene

Using the cDNA library obtained in (3) as a template, PCR was carried out by using a primer pair for obtaining GLD gene. As a result, PCR products considered to be internal sequences of the GLD gene were confirmed. Note that the primer pair comprises primers designed for obtaining various GLD genes on the basis of a plurality of GLD sequences which have been already clarified by the present inventors. The PCR products was purified, and ligated to T-vector PMD20 (TAKARA BIO INC.) by using DNA Ligation Kit (TAKARA BIO INC.).

Using the obtained plasmid vector, *Escherichia coli* JM109 competent cell (TAKARA BIO INC.) was transformed by a known method. A plasmid vector was extracted/purified from the obtained transformant by using NucleoSpin Plasmid QuickPure (TAKARA BIO INC.) to determine a base sequence of an insert. On the basis of the determined base sequence, a primer for clarifying upstream and downstream sequences of each GLD gene was designed. Using these primers, the whole length of the GLD gene from an initiation codon to a termination codon, 1758 bases was clarified by a 5' RACE method and a 3' RACE method. The gene sequence was represented by SEQ ID NO: 1.

(5) Preparation of Plasmid Vector for Expression Containing the Wild-Type GLD Gene A plasmid vector was prepared using an amylase-based modified promoter derived from *Aspergillus oryzae* described in Known Document 1 (heterologous gene expression system of *Aspergillus*, Toshitaka MINETOKI, Chemistry and Biology, 38, 12, 831-838, 2000). Finally, the prepared GLD gene represented by SEQ ID NO: 1 was bound to the downstream of the promoter to make a plasmid vector on which the gene could be expressed.

Example 2

(Obtaining the Transformant Having a Modified OLD Gene into which a Site-Specific Mutation is Introduced)

The following oligonucleotide was designed and synthesized for introducing mutation into the GLD gene. These base sequences were determined based on the base sequence of SEQ ID NO: 1.

```
Primer S71D (SEQ ID NO: 4):
5'-ACGTGACCAGCCCCGACGGCTACGGACTGGCCTTTGG-3'

Primer G72A (SEQ ID NO: 5):
5'-CAGCCCCTCTGCCTACGGACTGGCCTTTGGTACCG-3'

Primer Q169C (SEQ ID NO: 6):
5'-ACCTACATCCCTGAGTGCCACGGTACCTCTGGTCCTCTC-3'

Primer G183K (SEQ ID NO: 7):
5'-GTCGGCTGGAAGTCCAAGGGTGTCGAGAAGTCCTTCGTC-3'

Primer S188V (SEQ ID NO: 8):
5'-GGCGGTGTCGAGAAGGTTTTCGTCGACGTCTTGAACCAG-3'

Primer G210C (SEQ ID NO: 9):
5'-CTGAAGGACATTGCTTGCGGAGACATGGTCGGCTGGGAAC-3'

Primer A221Y (SEQ ID NO: 10):
5'-CTGGAACATCTACCCCTACACCCTGGACACTGCTCTTC-3'

Primer S269V (SEQ ID NO: 11):
5'-GCTGAGGCCACCGCCGTTGGAGTTCTCGTCAAGGACAAG-3'

Primer N346K (SEQ ID NO: 12):
5'-CAGACCAGCTCCAAGAAATTCACCGGTGTCACCACCTTC-3'

Primer S427V (SEQ ID NO: 13):
5'-ACCCCTGCCGGTTCTGTTTTCTCCACCGAGTACTGGGCC-3'

Primer S429V (SEQ ID NO: 14):
5'-GCCGGTTCTTCCTTCGTTACCGAGTACTGGGCCCTCCTG-3'

Primer F521W (SEQ ID NO: 15):
5'-GAACTACCGCTCCAACTGGCACCCCGTCGGCACCAC-3'

Primer F521Y (SEQ ID NO: 16):
5'-AACTACCGCTCCAACTATCACCCCGTCGGCACCACCGCC-3'

Primer V567A (SEQ ID NO: 17):
5'-ITTGCGGCCACCITGCCTCCACTCTCTACGCCATTGCC-3'

Primer V567G (SEQ ID NO: 18):
:5'-GTTTGCGGCCACCTTGGGTCCACTCTCTACGCCATTGCC-3'

Primer V567M (SEQ ID NO: 19):
5'-GTTTGCGGCCACCITATGTCCACTCTCTACGCCATTGCC-3'

Primer V567Q (SEQ ID NO: 20):
5'-GTTTGCGGCCACCTTCAGTCCACTCTCTACGCCATTGCC-3'

Primer V567S (SEQ ID NO: 21):
5'-GTTTGCGGCCACCTTAGCTCCACTCTCTACGCCATTGCC-3'

Primer V567T (SEQ ID NO: 22):
5'-GTTTGCGGCCACCTTACGTCCACTCTCTACGCCATTGCC-3'

Primer V567C (SEQ ID NO: 23):
5'-GTTTGCGGCCACCTTTGTTCCACTCTCTACGCCATTGCC-3'
```

The plasmid containing the wild-type GLD gene (SEQ ID NO: 1) obtained in Example 1, the primer synthesized in Example 2, and an oligonucleotide complementary to the primer were used to obtain a plasmid into which mutation was introduced using QuikChangeII Site-Directed Mutagenesis Kit (Stratagene Corp.) according to an experiment procedure appended to the kit. The prepared plasmid was used to transform *Escherichia coli* JM109 strain (TAKARA BIO INC.). Then, the resulting transformant was cultured, and the plasmid was extracted from the collected fungus body using illustra plasmidPrep Midi Flow Kit (GE Healthcare).

Using the extracted plasmid, a recombinant mold (*Aspergillus oryzae*) which produces each of recombinant GLD was produced according to methods described in Known Document 2 (Biosci. Biotech. Biochem., 61 (8), 1367-1369, 1997) and Known Document 3 (genetic engineering technique for koji-mold for sake, Katsuya GOMI, journal of Brewing Society of Japan, 494-502, 2000). The obtained recombinant strain was refined in Czapek-Dox solid medium. An *Aspergillus oryzae* NS4 strain was used as a host. This strain is available as those being sold in lots at National Research Institute of Brewing, which is Incorporated Administrative Agency.

Finally obtained were: a transformant (mold) producing the wild-type GLD; and transformants (mold) producing the modified GLDs which have amino acid substitution of S71D, N346K, S429V, F521W, V567A, V567C, V567G, V567M, V567Q, V567S, V567T, Q169C+G210C, G183K+V567A, S71 D+V567C, G72A+V567C, A221Y+V567C, S269V+V567C, F521W+V567C, G72A+S188V+V567C, G72A+A221Y+V567C, G72A+S427V+V567C, G72A+F521W+V567C, G72A+F521Y+V567C, 072A+Q169C+G210C, Q169C+G210C+V567C, Q169C+G210C+F521W, Q169C+G210C+F521Y, S188V+F521W+V567C, A221Y+F521W+V567C, or S71D+G72A+F521 W+V567C, respectively.

Example 3

(Evaluation of Thermal Stability of Each Modified OLD)

10 mL of a liquid medium consisting of 2% (w/v) of Pinedex (Matsutani Chemical Industry Co., Ltd.), 1% (w/v) of tryptone (Becton, Dickinson and Company), 0.5% (w/v) of potassium dihydrogenphosphate (Wako Pure Chemical Industries, Ltd.), 0.05% (w/v) of magnesium sulfate heptahydrate (NACALAI TESQUE, INC.) and water was was introduced into a big test tube (22 mm×200 mm) and autoclaved at 121° C. for 20 minutes. Each of the transformants obtained in Example 2 was inoculated to the cooled liquid medium and shake-cultured at 30° C. for 4 days. After completion of the culture, the supernatant was collected by centrifugation, GLD activity was measured by the above-mentioned method for measuring GLD activity, and as a result, the GLD activity could be confirmed.

Each of the resultant supernatants were diluted to about 6.6 U/mL, and then 1M phosphate buffer (pH 6.0) was added thereto so that the final concentration was 0.1 M. Each sample was treated at 45° C. for 30 minutes. The enzyme activity of each sample before and after the treatment was measured by the above-mentioned GLD activity measurement method. A ratio of a post-treatment activity value with respect to a pre-treatment activity value was calculated as residual activity (%), and a ratio of the residual activity of each modified GLD with respect to residual activity of the wild-type GLD was calculated. These ratios are shown in Tables 2 to 6.

TABLE 2

| amino acid substitution | percentage of residual activity of the modified glucose dehydrogenase with respect to that of the wild-type enzyme (%) |
|---|---|
| (wild-type) | 100 |
| N 3 4 6 K | 113 |
| S 4 2 9 V | 111 |
| V 5 6 7 C | 159 |

TABLE 3

| amino acid substitution | percentage of residual activity of the modified glucose dehydrogenase with respect to that of the wild-type enzyme (%) |
|---|---|
| (wild-type) | 100 |
| S 7 1 D | 113 |
| G 1 8 3 K, V 5 6 7 A | 115 |

TABLE 4

| amino acid substitution | percentage of residual activity of the modified glucose dehydrogenase with respect to that of the wild-type enzyme (%) |
|---|---|
| (wild-type) | 100 |
| G 7 2 A, V 5 6 7 C | 156 |
| S 2 6 9 V, V 5 6 7 C | 143 |
| F 5 2 1 W, V 5 6 7 C | 159 |

TABLE 5

| amino acid substitution | percentage of residual activity of the modified glucose dehydrogenase with respect to that of the wild-type enzyme (%) |
|---|---|
| (wild-type) | 100 |
| V 5 6 7 A | 160 |
| V 5 6 7 G | 156 |
| V 5 6 7 M | 104 |
| V 5 6 7 Q | 102 |
| V 5 6 7 S | 151 |
| V 5 6 7 T | 122 |

TABLE 5-continued

| amino acid substitution | percentage of residual activity of the modified glucose dehydrogenase with respect to that of the wild-type enzyme (%) |
|---|---|
| Q 1 6 9 C, G 2 1 0 C | 172 |
| Q 1 6 9 C, G 2 1 0 C, V 5 6 7 C | 184 |
| G 7 2 A, F 5 2 1 W, V 5 6 7 C | 159 |

TABLE 6

| amino acid substitution | percentage of residual activity of the modified glucose dehydrogenase with respect to that of the wild-type enzyme (%) |
|---|---|
| (wild-type) | 100 |
| F 5 2 1 W | 118 |
| S 7 1 D, V 5 6 7 C | 140 |
| A 2 2 1 Y, V 5 6 7 C | 148 |
| G 7 2 A, S 1 8 8 V, V 5 6 7 C | 152 |
| G 7 2 A, A 2 2 1 Y, V 5 6 7 C | 173 |
| G 7 2 A, S 4 2 7 V, V 5 6 7 C | 141 |
| G 7 2 A, F 5 2 1 V, V 5 6 7 C | 143 |
| S 1 8 8 V, F 5 2 1 W, V 5 6 7 C | 154 |
| A 2 2 1 Y, F 5 2 1 W, V 5 6 7 C | 163 |
| G 7 2 A, Q 1 6 9 C, G 2 1 0 C | 154 |
| Q 1 6 9 C, G 2 1 0 C, F 5 2 1 W | 144 |
| Q 1 6 9 C, G 2 1 0 C, F 5 2 1 Y | 165 |
| S 7 1 D, G 7 2 A, F 5 2 1 W, V 5 6 7 C | 147 |

From the above, for the residual activities before and after the treatment in 0.1M phosphate buffer (pH 6.0) at 45° C. for 30 minutes, it was found that all of the above-mentioned modified GLDs had residual activity higher than that of the wild-type GLD. That is, all of the above-mentioned modified GLD had improved thermal stability compared to the wild-type GLD. More specifically, assuming that the residual activity (%) of the wild-type is 100: residual activity of modified V567Q and V567M was more than 100; residual activity of modified S71D, N346K, S429V, F521W and G183K+V567A was 110 or more; residual activity of modified V567T was 120 or more; residual activity of modified S71D+V567C, A221Y+V567C, S269V+V567C, G72A+S427V+V567C, G72A+F521Y+V567C, Q169C+G210C+F521W and S71D+G72A+F521W+V567C was 140 or more; residual activity of modified V567C, V567G, V567S, G72A+V567C, G72A+S188V+V567C, G72A+Q169C+G210C, G72A+F521W+V567C and S188V+F521W+V567C was 150 or more; residual activity of modified V567A, F521W+V567C, A221Y+F521W+V567C and Q169C+G210C+F521 Y was 160 or more; and residual activity of modified Q169C+G210C, G72A|A221Y|V567C, Q169C|G210C|V567C was 170 or more.

INDUSTRIAL APPLICABILITY

The present invention makes it possible to utilize a modified glucose dehydrogenase with excellent thermal stability. Furthermore, the modified glucose dehydrogenase according to the present invention can be efficiently manufactured so that a biosensor manufacturing process including a heating step can be stably carried out.

The invention claimed is:

1. A modified glucose dehydrogenase selected from the group consisting of consisting of
    an amino acid sequence represented by SEQ ID NO: 2 and at least one amino acid substitution at a position corresponding to S71, G72, Q169, S188, G210, A221, S269, N346, S427, S429, F521 or V567 of SEQ ID NO: 2;
    an amino acid sequence represented by SEQ ID NO: 3 and at least one amino acid substitution at a position corresponding to S71, G72, Q169, S188, G210, A221, S269, N346, S427, S429, F521 or V567 of SEQ ID NO: 2;
    an amino acid sequence represented by SEQ ID NO: 24 and at least one amino acid substitution at a position corresponding to S71, G72, Q169, S188, G210, A221, S269, N346, S427, S429, F521 or V567 of SEQ ID NO: 2;
    an amino acid sequence represented by SEQ ID NO: 25 and at least one amino acid substitution at a position corresponding to S71, G72, Q169, S188, G210, A221, S269, N346, S427, S429, F521 or V567 of SEQ ID NO: 2;
    an amino acid sequence represented by SEQ ID NO: 26 and at least one amino acid substitution at a position corresponding to S71, G72, Q169, S188, G210, A221, S269, N346, S427, S429, F521 or V567 of SEQ ID NO: 2;
    an amino acid sequence represented by SEQ ID NO: 27 and at least one amino acid substitution at a position corresponding to S71, G72, Q169, S188, G210, A221, S269, N346, S427, S429, F521 or V567 of SEQ ID NO: 2; and
    an amino acid sequence represented by SEQ ID NO: 28 and at least one amino acid substitution at a position corresponding to S71, G72, Q169, S188, G210, A221, S269, N346, S427, S429, F521 or V567 of SEQ ID NO: 2;
    wherein the modified glucose dehydrogenase has, after a treatment in 0.1M phosphate buffer (pH 6.0) at 45° C. for 30 minutes, a residual activity greater than that of a wild-type enzyme.

2. The modified glucose dehydrogenase according to claim 1, wherein the at least one amino acid substitution is S71G, S71N, S71D, G72A, Q169Y, Q169F, Q169C, G183N, G183K, S188V, G210C, A221S, A221Y, S269V, N346K, N346A, S427A, S427V, S429V, F521W, F521Y, V567A, V567C, V567G, V567M, V567Q, V567S, or V567T.

3. A polynucleotide encoding the modified glucose dehydrogenase according to claim 1.

4. A recombinant vector containing the polynucleotide according to claim 3.

5. A cell transformed using the vector according to claim 4.

6. A method for manufacturing a modified glucose dehydrogenase, wherein the cell according to claim 5 is cultured, and the modified glucose dehydrogenase is collected from a resultant culture.

7. A method for measuring glucose comprising:
contacting a test sample containing glucose with the modified glucose dehydrogenase according to claim 1.

8. A reagent composition for measuring glucose containing the modified glucose dehydrogenase according to claim 1.

9. A biosensor for measuring glucose containing
a modified glucose dehydrogenase selected from the group consisting of:
an amino acid sequence represented by SEQ ID NO: 2 and at least one amino acid substitution at a position corresponding to S71, G72, Q169, S188, G210, A221, S269, N346, S427, S429, F521 or V567 of SEQ ID NO: 2;
an amino acid sequence represented by SEQ ID NO: 3 and at least one amino acid substitution at a position corresponding to S71, G72, Q169, S188, G210, A221, S269, N346, S427, S429, F521 or V567 of SEQ ID NO: 2;
an amino acid sequence represented by SEQ ID NO: 24 and at least one amino acid substitution at a position corresponding to S71, G72, Q169, S188, G210, A221, S269, N346, S427, S429, F521 or V567 of SEQ ID NO: 2;
an amino acid sequence represented by SEQ ID NO: 25 and at least one amino acid substitution at a position corresponding to S71, G72, Q169, S188, G210, A221, S269, N346, S427, S429, F521 or V567 of SEQ ID NO: 2;
an amino acid sequence represented by SEQ ID NO: 26 and at least one amino acid substitution at a position corresponding to S71, G72, Q169, S188, G210, A221, S269, N346, S427, S429, F521 or V567 of SEQ ID NO: 2;
an amino acid sequence represented by SEQ ID NO: 27 and at least one amino acid substitution at a position corresponding to S71, G72, Q169, S188, G210, A221, S269, N346, S427, S429, F521 or V567 of SEQ ID NO: 2; and
an amino acid sequence represented by SEQ ID NO: 28 and at least one amino acid substitution at a position corresponding to S71, G72, Q169, S188, G210, A221, S269, N346, S427, S429, F521 or V567 of SEQ ID NO: 2;
wherein the modified glucose dehydrogenase has, after a treatment in 0.1M phosphate buffer (pH 6.0) at 45° C. for 30 minutes, a residual activity greater than that of a wild-type enzyme.

10. The biosensor of claim 9, wherein the at least one amino acid substitution is S71G, S71N, S71D, G72A, Q169Y, Q169F, Q169C, G183N, G183K, S188V, G210C, A221S, A221Y, S269V, N346K, N346A, S427A, S427V, S429V, F521W, F521Y, V567A, V567C, V567G, V567M, V567Q, V567S, or V567T.

11. A modified glucose dehydrogenase consisting of
an amino acid sequence having at least 99% identity to the amino acid sequence represented by SEQ ID NO: 2, 3, 24, 25, 26, 27 or 28, and containing at least one amino acid substitution at positions corresponding to S71, G72, Q169, G183, S188, G210, A221, S269, N346, S427, S429, F521 or V567 in the amino acid sequence represented by SEQ ID NO: 2,
wherein the modified glucose dehydrogenase has, after a treatment in 0.1M phosphate buffer (pH 6.0) at 45° C. for 30 minutes, a residual activity greater than that of a wild-type enzyme.

12. The modified glucose dehydrogenase according to claim 11, wherein the at least one amino acid substitution is S71G, S71N, S71D, G72A, Q169Y, Q169F, Q169C, G183N, G183K, S188V, G210C, A221S, A221Y, S269V, N346K, N346A, S427A, S427V, S429V, F521W, F521Y, V567A, V567C, V567G, V567M, V567Q, V567S, or V567T.

13. A polynucleotide encoding the modified glucose dehydrogenase according to claim 11.

14. A recombinant vector containing the polynucleotide according to claim 13.

15. A cell transformed using the vector according to claim 14.

16. A method for manufacturing a modified glucose dehydrogenase, wherein the cell according to claim 15 is cultured, and the modified glucose dehydrogenase is collected from a resultant culture.

17. A method for measuring glucose comprising:
contacting a test sample containing glucose with the modified glucose dehydrogenase according to claim 11.

18. A reagent composition for measuring glucose containing the modified glucose dehydrogenase according to claim 11.

19. A biosensor for measuring glucose, comprising:
a modified glucose dehydrogenase consisting of an amino acid sequence having at least 99% identity to the amino acid sequence represented by SEQ ID NO: 2, 3, 24, 25, 26, 27 or 28, and containing at least one amino acid substitution at positions corresponding to S71, G72, Q169, G183, S188, G210, A221, S269, N346, S427, S429, F521 or V567 in the amino acid sequence represented by SEQ ID NO: 2,
wherein the modified glucose dehydrogenase has, after a treatment in 0.1M phosphate buffer (pH 6.0) at 45° C. for 30 minutes, a residual activity greater than that of a wild-type enzyme.

20. The biosensor according to claim 19, wherein the at least one amino acid substitution is S71G, S71N, S71D, G72A, Q169Y, Q169F, Q169C, G183N, G183K, S188V, G210C, A221S, A221Y, S269V, N346K, N346A, S427A, S427V, S429V, F521W, F521Y, V567A, V567C, V567G, V567M, V567Q, V567S, or V567T.

* * * * *

UNITED STATES PATENT AND TRADEMARK OFFICE
CERTIFICATE OF CORRECTION

| | |
|---|---|
| PATENT NO. | : 11,725,193 B2 |
| APPLICATION NO. | : 16/619637 |
| DATED | : August 15, 2023 |
| INVENTOR(S) | : Michinari Honda et al. |

It is certified that error appears in the above-identified patent and that said Letters Patent is hereby corrected as shown below:

In the Claims

<u>In Column 47, Line 42, change:</u>
"1. A modified glucose dehydrogenase selected from the group consisting of consisting of"
To:
--1. A modified glucose dehydrogenase selected from the group consisting of--

Signed and Sealed this
Twenty-fifth Day of March, 2025

Coke Morgan Stewart
*Acting Director of the United States Patent and Trademark Office*

SEQUENCE LISTING

<160> NUMBER OF SEQ ID NOS: 28

<210> SEQ ID NO 1
<211> LENGTH: 1758
<212> TYPE: DNA
<213> ORGANISM: Glomerella fructigena NBRC5951
<220> FEATURE:
<221> NAME/KEY: CDS
<222> LOCATION: (1)..(1758)
<220> FEATURE:
<221> NAME/KEY: sig_peptide
<222> LOCATION: (1)..(63)

<400> SEQUENCE: 1

| | | | | | | | | | | | | | | | | |
|---|---|---|---|---|---|---|---|---|---|---|---|---|---|---|---|---|
| atg | ctg | cgc | tcc | att | gtc | tcc | ctc | ccg | ctt | ctt | gcg | gcc | acc | gcg | ctc | 48 |
| Met | Leu | Arg | Ser | Ile | Val | Ser | Leu | Pro | Leu | Leu | Ala | Ala | Thr | Ala | Leu | |
| 1 | | | | 5 | | | | | 10 | | | | | 15 | | |

| gcc | tat | ccc | gct | gca | tct | tcg | cag | cgc | ttc | gac | tat | gtc | att | atc | ggt | 96 |
|---|---|---|---|---|---|---|---|---|---|---|---|---|---|---|---|---|
| Ala | Tyr | Pro | Ala | Ala | Ser | Ser | Gln | Arg | Phe | Asp | Tyr | Val | Ile | Ile | Gly | |
| | | | 20 | | | | | 25 | | | | | 30 | | | |

| ggt | ggt | acc | agc | ggt | ctc | gtc | gtt | gcc | aac | cgt | ctt | tcc | gag | ttg | aac | 144 |
|---|---|---|---|---|---|---|---|---|---|---|---|---|---|---|---|---|
| Gly | Gly | Thr | Ser | Gly | Leu | Val | Val | Ala | Asn | Arg | Leu | Ser | Glu | Leu | Asn | |
| | | | 35 | | | | | 40 | | | | | 45 | | | |

| aat | gtc | acc | gtc | gct | gtc | att | gag | gcc | ggt | gac | tct | gtc | tac | gac | aac | 192 |
|---|---|---|---|---|---|---|---|---|---|---|---|---|---|---|---|---|
| Asn | Val | Thr | Val | Ala | Val | Ile | Glu | Ala | Gly | Asp | Ser | Val | Tyr | Asp | Asn | |
| 50 | | | | | 55 | | | | | 60 | | | | | | |

| gac | aac | gtg | acc | agc | ccc | tct | ggc | tac | gga | ctg | gcc | ttt | ggt | acc | gac | 240 |
|---|---|---|---|---|---|---|---|---|---|---|---|---|---|---|---|---|
| Asp | Asn | Val | Thr | Ser | Pro | Ser | Gly | Tyr | Gly | Leu | Ala | Phe | Gly | Thr | Asp | |
| 65 | | | | 70 | | | | | 75 | | | | | 80 | | |

| atc | gac | tac | gcc | tat | cag | act | act | gcc | cag | aag | tat | ggc | ggc | aac | aag | 288 |
|---|---|---|---|---|---|---|---|---|---|---|---|---|---|---|---|---|
| Ile | Asp | Tyr | Ala | Tyr | Gln | Thr | Thr | Ala | Gln | Lys | Tyr | Gly | Gly | Asn | Lys | |
| | | | | 85 | | | | | 90 | | | | | 95 | | |

| act | cag | acc | ctc | cgt | gcc | ggc | aag | gct | ctc | ggc | ggt | acc | agc | acc | atc | 336 |
|---|---|---|---|---|---|---|---|---|---|---|---|---|---|---|---|---|
| Thr | Gln | Thr | Leu | Arg | Ala | Gly | Lys | Ala | Leu | Gly | Gly | Thr | Ser | Thr | Ile | |
| | | | 100 | | | | | 105 | | | | | 110 | | | |

| aac | ggc | atg | gct | tac | acc | cgt | gct | cag | gac | gtt | cag | atc | gac | atc | tgg | 384 |
|---|---|---|---|---|---|---|---|---|---|---|---|---|---|---|---|---|
| Asn | Gly | Met | Ala | Tyr | Thr | Arg | Ala | Gln | Asp | Val | Gln | Ile | Asp | Ile | Trp | |
| | | 115 | | | | | 120 | | | | | 125 | | | | |

| gag | cgt | ctt | ggc | aac | gac | ggc | tgg | aac | tgg | aac | aac | ctc | ctc | aag | tac | 432 |
|---|---|---|---|---|---|---|---|---|---|---|---|---|---|---|---|---|
| Glu | Arg | Leu | Gly | Asn | Asp | Gly | Trp | Asn | Trp | Asn | Asn | Leu | Leu | Lys | Tyr | |
| | 130 | | | | | 135 | | | | | 140 | | | | | |

| tac | aag | aag | tcc | gag | act | ctc | cag | ccc | ccc | acc | gtc | cag | gtt | gac | 480 |
|---|---|---|---|---|---|---|---|---|---|---|---|---|---|---|---|
| Tyr | Lys | Lys | Ser | Glu | Thr | Leu | Gln | Pro | Pro | Thr | Thr | Val | Gln | Val | Asp |
| 145 | | | | | 150 | | | | | 155 | | | | | 160 |

| gat | ggc | gtc | acc | tac | atc | cct | gag | cag | cac | ggt | acc | tct | ggt | cct | ctc | 528 |
|---|---|---|---|---|---|---|---|---|---|---|---|---|---|---|---|---|
| Asp | Gly | Val | Thr | Tyr | Ile | Pro | Glu | Gln | His | Gly | Thr | Ser | Gly | Pro | Leu | |
| | | | 165 | | | | | 170 | | | | | 175 | | | |

| aag | gtc | ggc | tgg | aag | tcc | ggc | ggt | gtc | gag | aag | tcc | ttc | gtc | gac | gtc | 576 |
|---|---|---|---|---|---|---|---|---|---|---|---|---|---|---|---|---|
| Lys | Val | Gly | Trp | Lys | Ser | Gly | Gly | Val | Glu | Lys | Ser | Phe | Val | Asp | Val | |
| | | 180 | | | | | 185 | | | | | 190 | | | | |

| ttg | aac | cag | acc | tac | aat | gcc | gtt | ggc | gtc | cct | gcc | ctg | aag | gac | att | 624 |
|---|---|---|---|---|---|---|---|---|---|---|---|---|---|---|---|---|
| Leu | Asn | Gln | Thr | Tyr | Asn | Ala | Val | Gly | Val | Pro | Ala | Leu | Lys | Asp | Ile | |
| | 195 | | | | | 200 | | | | | 205 | | | | | |

| gct | ggt | gga | gac | atg | gtc | ggc | tgg | aac | atc | tac | ccc | gcc | acc | ctg | gac | 672 |
|---|---|---|---|---|---|---|---|---|---|---|---|---|---|---|---|---|
| Ala | Gly | Gly | Asp | Met | Val | Gly | Trp | Asn | Ile | Tyr | Pro | Ala | Thr | Leu | Asp | |
| 210 | | | | | 215 | | | | | 220 | | | | | | |

| act | gct | ctt | cag | gtt | cgc | gat | gat | gct | gcc | cgc | gcg | tac | tac | ttc | ccc | 720 |
|---|---|---|---|---|---|---|---|---|---|---|---|---|---|---|---|---|
| Thr | Ala | Leu | Gln | Val | Arg | Asp | Asp | Ala | Ala | Arg | Ala | Tyr | Tyr | Phe | Pro | |
| 225 | | | | 230 | | | | | 235 | | | | | 240 | | |

| tac | cag | aac | cgc | acc | aac | ttc | cgc | gtc | ttc | ttg | aac | acc | gag | gct | cag | 768 |
|---|---|---|---|---|---|---|---|---|---|---|---|---|---|---|---|---|
| Tyr | Gln | Asn | Arg | Thr | Asn | Phe | Arg | Val | Phe | Leu | Asn | Thr | Glu | Ala | Gln | |
| | | | | 245 | | | | | 250 | | | | | 255 | | |

-continued

| | |
|---|---|
| aaa ctc gtc tgg gct gag gga gct gag gcc acc gcc tcc gga gtt ctc<br>Lys Leu Val Trp Ala Glu Gly Ala Glu Ala Thr Ala Ser Gly Val Leu<br>260                        265                    270 | 816 |
| gtc aag gac aag acc ggt gct acc cac acc gtc tat gcc aac aag gag<br>Val Lys Asp Lys Thr Gly Ala Thr His Thr Val Tyr Ala Asn Lys Glu<br>      275                    280                    285 | 864 |
| gtc att ctc tct gct ggc tct ctc aga tct cct ctc ctg gag cag<br>Val Ile Leu Ser Ala Gly Ser Leu Arg Ser Pro Leu Leu Glu Gln<br>290                        295                    300 | 912 |
| tcc ggt gta gga aac ccc gag atc ctg aag gcc gcc ggc atc cag act<br>Ser Gly Val Gly Asn Pro Glu Ile Leu Lys Ala Ala Gly Ile Gln Thr<br>305                    310                    315                  320 | 960 |
| aag ctc aac ctc ccc acc gtc ggt gag aac ctc cag gac cag atg aac<br>Lys Leu Asn Leu Pro Thr Val Gly Glu Asn Leu Gln Asp Gln Met Asn<br>                    325                    330                  335 | 1008 |
| aac ggc ctc gcc cag acc agc tcc aag aac ttc acc ggt gtc acc acc<br>Asn Gly Leu Ala Gln Thr Ser Ser Lys Asn Phe Thr Gly Val Thr Thr<br>340                        345                    350 | 1056 |
| ttc gtt gcc tac ccc aac gtc gac gac gtc ttc gca aac cag acc gct<br>Phe Val Ala Tyr Pro Asn Val Asp Asp Val Phe Ala Asn Gln Thr Ala<br>                    355                    360                  365 | 1104 |
| tcc ctc gct gcc aac atc aag acc cag ctc tcc cag tgg gcc gac cag<br>Ser Leu Ala Ala Asn Ile Lys Thr Gln Leu Ser Gln Trp Ala Asp Gln<br>370                        375                    380 | 1152 |
| gtc tcc gag tac acc aaa ggc gtc gtc acc aag gag cag ctc aac aag<br>Val Ser Glu Tyr Thr Lys Gly Val Val Thr Lys Glu Gln Leu Asn Lys<br>385                        390                    395                  400 | 1200 |
| ttc ttc gac atc cag tac gac ctc atc ttc acc gac aag gtc ccc ctc<br>Phe Phe Asp Ile Gln Tyr Asp Leu Ile Phe Thr Asp Lys Val Pro Leu<br>                    405                    410                  415 | 1248 |
| gct gag atc ctg atc acc cct gcc ggt tct tcc ttc tcc acc gag tac<br>Ala Glu Ile Leu Ile Thr Pro Ala Gly Ser Ser Phe Ser Thr Glu Tyr<br>420                        425                    430 | 1296 |
| tgg gcc ctc ctg ccc ttc gct cgc ggc aac atc cat gtc acc ggc gcc<br>Trp Ala Leu Leu Pro Phe Ala Arg Gly Asn Ile His Val Thr Gly Ala<br>                    435                    440                  445 | 1344 |
| aac tcc tct gct gcc aag atc aac ccc aac tac ttc atg atg gac tgg<br>Asn Ser Ser Ala Ala Lys Ile Asn Pro Asn Tyr Phe Met Met Asp Trp<br>450                        455                    460 | 1392 |
| gac atg acc gag cag att ggc acc gcc aag ttc atc cgt cag ctg tac<br>Asp Met Thr Glu Gln Ile Gly Thr Ala Lys Phe Ile Arg Gln Leu Tyr<br>465                        470                    475                  480 | 1440 |
| aag act gcc cct ctg agc cag tac ttc gcc agc gag acc aag cct ggt<br>Lys Thr Ala Pro Leu Ser Gln Tyr Phe Ala Ser Glu Thr Lys Pro Gly<br>                    485                    490                  495 | 1488 |
| ttg gcc acc atc gcc gag gac gcc tct gac gat gtt tgg tcc aag tgg<br>Leu Ala Thr Ile Ala Glu Asp Ala Ser Asp Asp Val Trp Ser Lys Trp<br>500                        505                    510 | 1536 |
| atc ctt gag aac tac cgc tcc aac ttc cac ccc gtc ggc acc acc gcc<br>Ile Leu Glu Asn Tyr Arg Ser Asn Phe His Pro Val Gly Thr Thr Ala<br>                    515                    520                  525 | 1584 |
| atg atg tca aag gag ctg ggc ggt gtt gtc gat gcc aac ctc aag gtc<br>Met Met Ser Lys Glu Leu Gly Gly Val Val Asp Ala Asn Leu Lys Val<br>530                        535                    540 | 1632 |
| tac ggc acc agc aac gtc cgc gtc gtc gat gcc ggt gtc ctg cct ttc<br>Tyr Gly Thr Ser Asn Val Arg Val Val Asp Ala Gly Val Leu Pro Phe<br>545                        550                    555                  560 | 1680 |
| cag gtt tgc ggc cac ctt gtg tcc act ctc tac gcc att gcc gag aag<br>Gln Val Cys Gly His Leu Val Ser Thr Leu Tyr Ala Ile Ala Glu Lys | 1728 |

```
                        565                 570                 575
gct tcg gac atc atc aag gct tcc gcc tag                               1758
Ala Ser Asp Ile Ile Lys Ala Ser Ala
                        580                 585
```

<210> SEQ ID NO 2
<211> LENGTH: 585
<212> TYPE: PRT
<213> ORGANISM: Glomerella fructigena NBRC5951

<400> SEQUENCE: 2

```
Met Leu Arg Ser Ile Val Ser Leu Pro Leu Leu Ala Ala Thr Ala Leu
1               5                   10                  15

Ala Tyr Pro Ala Ala Ser Ser Gln Arg Phe Asp Tyr Val Ile Ile Gly
                20                  25                  30

Gly Gly Thr Ser Gly Leu Val Val Ala Asn Arg Leu Ser Glu Leu Asn
            35                  40                  45

Asn Val Thr Val Ala Val Ile Glu Ala Gly Asp Ser Val Tyr Asp Asn
        50                  55                  60

Asp Asn Val Thr Ser Pro Ser Gly Tyr Gly Leu Ala Phe Gly Thr Asp
65                  70                  75                  80

Ile Asp Tyr Ala Tyr Gln Thr Thr Ala Gln Lys Tyr Gly Gly Asn Lys
                85                  90                  95

Thr Gln Thr Leu Arg Ala Gly Lys Ala Leu Gly Gly Thr Ser Thr Ile
                100                 105                 110

Asn Gly Met Ala Tyr Thr Arg Ala Gln Asp Val Gln Ile Asp Ile Trp
            115                 120                 125

Glu Arg Leu Gly Asn Asp Gly Trp Asn Trp Asn Asn Leu Leu Lys Tyr
130                 135                 140

Tyr Lys Lys Ser Glu Thr Leu Gln Pro Pro Thr Thr Val Gln Val Asp
145                 150                 155                 160

Asp Gly Val Thr Tyr Ile Pro Glu Gln His Gly Thr Ser Gly Pro Leu
                165                 170                 175

Lys Val Gly Trp Lys Ser Gly Gly Val Glu Lys Ser Phe Val Asp Val
            180                 185                 190

Leu Asn Gln Thr Tyr Asn Ala Val Gly Val Pro Ala Leu Lys Asp Ile
        195                 200                 205

Ala Gly Gly Asp Met Val Gly Trp Asn Ile Tyr Pro Ala Thr Leu Asp
    210                 215                 220

Thr Ala Leu Gln Val Arg Asp Asp Ala Ala Arg Ala Tyr Tyr Phe Pro
225                 230                 235                 240

Tyr Gln Asn Arg Thr Asn Phe Arg Val Phe Leu Asn Thr Glu Ala Gln
                245                 250                 255

Lys Leu Val Trp Ala Glu Gly Ala Glu Ala Thr Ala Ser Gly Val Leu
            260                 265                 270

Val Lys Asp Lys Thr Gly Ala Thr His Thr Val Tyr Ala Asn Lys Glu
        275                 280                 285

Val Ile Leu Ser Ala Gly Ser Leu Arg Ser Pro Leu Leu Leu Glu Gln
    290                 295                 300

Ser Gly Val Gly Asn Pro Glu Ile Leu Lys Ala Ala Gly Ile Gln Thr
305                 310                 315                 320

Lys Leu Asn Leu Pro Thr Val Gly Glu Asn Leu Gln Asp Gln Met Asn
                325                 330                 335

Asn Gly Leu Ala Gln Thr Ser Ser Lys Asn Phe Thr Gly Val Thr Thr
            340                 345                 350
```

-continued

Phe Val Ala Tyr Pro Asn Val Asp Asp Val Phe Ala Asn Gln Thr Ala
            355                 360                 365

Ser Leu Ala Ala Asn Ile Lys Thr Gln Leu Ser Gln Trp Ala Asp Gln
    370                 375                 380

Val Ser Glu Tyr Thr Lys Gly Val Val Thr Lys Glu Gln Leu Asn Lys
385                 390                 395                 400

Phe Phe Asp Ile Gln Tyr Asp Leu Ile Phe Thr Asp Lys Val Pro Leu
                405                 410                 415

Ala Glu Ile Leu Ile Thr Pro Ala Gly Ser Ser Phe Ser Thr Glu Tyr
                420                 425                 430

Trp Ala Leu Leu Pro Phe Ala Arg Gly Asn Ile His Val Thr Gly Ala
                435                 440                 445

Asn Ser Ser Ala Ala Lys Ile Asn Pro Asn Tyr Phe Met Met Asp Trp
    450                 455                 460

Asp Met Thr Glu Gln Ile Gly Thr Ala Lys Phe Ile Arg Gln Leu Tyr
465                 470                 475                 480

Lys Thr Ala Pro Leu Ser Gln Tyr Phe Ala Ser Glu Thr Lys Pro Gly
                485                 490                 495

Leu Ala Thr Ile Ala Glu Asp Ala Ser Asp Val Trp Ser Lys Trp
                500                 505                 510

Ile Leu Glu Asn Tyr Arg Ser Asn Phe His Pro Val Gly Thr Thr Ala
                515                 520                 525

Met Met Ser Lys Glu Leu Gly Gly Val Val Asp Ala Asn Leu Lys Val
    530                 535                 540

Tyr Gly Thr Ser Asn Val Arg Val Val Asp Ala Gly Val Leu Pro Phe
545                 550                 555                 560

Gln Val Cys Gly His Leu Val Ser Thr Leu Tyr Ala Ile Ala Glu Lys
                565                 570                 575

Ala Ser Asp Ile Ile Lys Ala Ser Ala
                580                 585

<210> SEQ ID NO 3
<211> LENGTH: 564
<212> TYPE: PRT
<213> ORGANISM: Glomerella fructibena NBRC5951
<220> FEATURE:
<221> NAME/KEY: PRT
<222> LOCATION: (1)..(564)

<400> SEQUENCE: 3

Ser Ser Gln Arg Phe Asp Tyr Val Ile Ile Gly Gly Gly Thr Ser Gly
1               5                   10                  15

Leu Val Val Ala Asn Arg Leu Ser Glu Leu Asn Asn Val Thr Val Ala
                20                  25                  30

Val Ile Glu Ala Gly Asp Ser Val Tyr Asp Asn Asp Asn Val Thr Ser
            35                  40                  45

Pro Ser Gly Tyr Gly Leu Ala Phe Gly Thr Asp Ile Asp Tyr Ala Tyr
        50                  55                  60

Gln Thr Thr Ala Gln Lys Tyr Gly Gly Asn Lys Thr Gln Thr Leu Arg
65                  70                  75                  80

Ala Gly Lys Ala Leu Gly Gly Thr Ser Thr Ile Asn Gly Met Ala Tyr
                85                  90                  95

Thr Arg Ala Gln Asp Val Gln Ile Asp Ile Trp Glu Arg Leu Gly Asn
                100                 105                 110

Asp Gly Trp Asn Trp Asn Asn Leu Leu Lys Tyr Tyr Lys Lys Ser Glu

-continued

```
                115                 120                 125
Thr Leu Gln Pro Pro Thr Thr Val Gln Val Asp Asp Gly Val Thr Tyr
    130                 135                 140
Ile Pro Glu Gln His Gly Thr Ser Gly Pro Leu Lys Val Gly Trp Lys
145                 150                 155                 160
Ser Gly Gly Val Glu Lys Ser Phe Val Asp Val Leu Asn Gln Thr Tyr
                165                 170                 175
Asn Ala Val Gly Val Pro Ala Leu Lys Asp Ile Ala Gly Gly Asp Met
            180                 185                 190
Val Gly Trp Asn Ile Tyr Pro Ala Thr Leu Asp Thr Ala Leu Gln Val
        195                 200                 205
Arg Asp Asp Ala Ala Arg Ala Tyr Tyr Phe Pro Tyr Gln Asn Arg Thr
    210                 215                 220
Asn Phe Arg Val Phe Leu Asn Thr Glu Ala Gln Lys Leu Val Trp Ala
225                 230                 235                 240
Glu Gly Ala Glu Ala Thr Ala Ser Gly Val Leu Val Lys Asp Lys Thr
                245                 250                 255
Gly Ala Thr His Thr Val Tyr Ala Asn Lys Glu Val Ile Leu Ser Ala
            260                 265                 270
Gly Ser Leu Arg Ser Pro Leu Leu Leu Glu Gln Ser Gly Val Gly Asn
        275                 280                 285
Pro Glu Ile Leu Lys Ala Ala Gly Ile Gln Thr Lys Leu Asn Leu Pro
    290                 295                 300
Thr Val Gly Glu Asn Leu Gln Asp Gln Met Asn Asn Gly Leu Ala Gln
305                 310                 315                 320
Thr Ser Ser Lys Asn Phe Thr Gly Val Thr Thr Phe Val Ala Tyr Pro
                325                 330                 335
Asn Val Asp Asp Val Phe Ala Asn Gln Thr Ala Ser Leu Ala Ala Asn
            340                 345                 350
Ile Lys Thr Gln Leu Ser Gln Trp Ala Asp Gln Val Ser Glu Tyr Thr
        355                 360                 365
Lys Gly Val Val Thr Lys Glu Gln Leu Asn Lys Phe Phe Asp Ile Gln
    370                 375                 380
Tyr Asp Leu Ile Phe Thr Asp Lys Val Pro Leu Ala Glu Ile Leu Ile
385                 390                 395                 400
Thr Pro Ala Gly Ser Ser Phe Ser Thr Glu Tyr Trp Ala Leu Leu Pro
                405                 410                 415
Phe Ala Arg Gly Asn Ile His Val Thr Gly Ala Asn Ser Ser Ala Ala
            420                 425                 430
Lys Ile Asn Pro Asn Tyr Phe Met Met Asp Trp Asp Met Thr Glu Gln
        435                 440                 445
Ile Gly Thr Ala Lys Phe Ile Arg Gln Leu Tyr Lys Thr Ala Pro Leu
    450                 455                 460
Ser Gln Tyr Phe Ala Ser Glu Thr Lys Pro Gly Leu Ala Thr Ile Ala
465                 470                 475                 480
Glu Asp Ala Ser Asp Asp Val Trp Ser Lys Trp Ile Leu Glu Asn Tyr
                485                 490                 495
Arg Ser Asn Phe His Pro Val Gly Thr Thr Ala Met Met Ser Lys Glu
            500                 505                 510
Leu Gly Gly Val Val Asp Ala Asn Leu Lys Val Tyr Gly Thr Ser Asn
        515                 520                 525
Val Arg Val Val Asp Ala Gly Val Leu Pro Phe Gln Val Cys Gly His
    530                 535                 540
```

-continued

Leu Val Ser Thr Leu Tyr Ala Ile Ala Glu Lys Ala Ser Asp Ile Ile
545                 550                 555                 560

Lys Ala Ser Ala

<210> SEQ ID NO 4
<211> LENGTH: 37
<212> TYPE: DNA
<213> ORGANISM: Artificial Sequence
<220> FEATURE:
<223> OTHER INFORMATION: primer_S71D
<220> FEATURE:
<221> NAME/KEY: DNA
<222> LOCATION: (1)..(35)

<400> SEQUENCE: 4
acgtgaccag ccccgacggc tacggactgg cctttgg                           37

<210> SEQ ID NO 5
<211> LENGTH: 35
<212> TYPE: DNA
<213> ORGANISM: Artificial Sequence
<220> FEATURE:
<223> OTHER INFORMATION: primer_G72A
<220> FEATURE:
<221> NAME/KEY: DNA
<222> LOCATION: (1)..(28)

<400> SEQUENCE: 5
cagcccctct gcctacggac tggcctttgg taccg                             35

<210> SEQ ID NO 6
<211> LENGTH: 39
<212> TYPE: DNA
<213> ORGANISM: Artificial Sequence
<220> FEATURE:
<223> OTHER INFORMATION: primer_Q169C
<220> FEATURE:
<221> NAME/KEY: DNA
<222> LOCATION: (1)..(34)

<400> SEQUENCE: 6
acctacatcc ctgagtgcca cggtacctct ggtcctctc                         39

<210> SEQ ID NO 7
<211> LENGTH: 39
<212> TYPE: DNA
<213> ORGANISM: Artificial Sequence
<220> FEATURE:
<223> OTHER INFORMATION: primer_G183K
<220> FEATURE:
<221> NAME/KEY: DNA
<222> LOCATION: (1)..(39)

<400> SEQUENCE: 7
gtcggctgga agtccaaggg tgtcgagaag tccttcgtc                         39

<210> SEQ ID NO 8
<211> LENGTH: 39
<212> TYPE: DNA
<213> ORGANISM: Artificial Sequence
<220> FEATURE:
<223> OTHER INFORMATION: primer_S188V
<220> FEATURE:
<221> NAME/KEY: DNA
<222> LOCATION: (1)..(39)

<400> SEQUENCE: 8
ggcggtgtcg agaaggtttt cgtcgacgtc ttgaaccag        39

<210> SEQ ID NO 9
<211> LENGTH: 39
<212> TYPE: DNA
<213> ORGANISM: Artificial Sequence
<220> FEATURE:
<223> OTHER INFORMATION: primer_G210C
<220> FEATURE:
<221> NAME/KEY: DNA
<222> LOCATION: (1)..(39)

<400> SEQUENCE: 9
ctgaaggaca ttgcttgcgg agacatggtc ggctggaac        39

<210> SEQ ID NO 10
<211> LENGTH: 38
<212> TYPE: DNA
<213> ORGANISM: Artificial Sequence
<220> FEATURE:
<223> OTHER INFORMATION: primer_A221Y
<220> FEATURE:
<221> NAME/KEY: DNA
<222> LOCATION: (1)..(38)

<400> SEQUENCE: 10
ctggaacatc taccccataca ccctggacac tgctcttc        38

<210> SEQ ID NO 11
<211> LENGTH: 39
<212> TYPE: DNA
<213> ORGANISM: Artificial Sequence
<220> FEATURE:
<223> OTHER INFORMATION: primer_S269V
<220> FEATURE:
<221> NAME/KEY: DNA
<222> LOCATION: (1)..(39)

<400> SEQUENCE: 11
gctgaggcca ccgccgttgg agttctcgtc aaggacaag        39

<210> SEQ ID NO 12
<211> LENGTH: 39
<212> TYPE: DNA
<213> ORGANISM: Artificial Sequence
<220> FEATURE:
<223> OTHER INFORMATION: primer_N346K
<220> FEATURE:
<221> NAME/KEY: DNA
<222> LOCATION: (1)..(39)

<400> SEQUENCE: 12
cagaccagct ccaagaaatt caccggtgtc accaccttc        39

<210> SEQ ID NO 13
<211> LENGTH: 39
<212> TYPE: DNA
<213> ORGANISM: Artificial Sequence
<220> FEATURE:
<223> OTHER INFORMATION: primer_S427V
<220> FEATURE:
<221> NAME/KEY: DNA
<222> LOCATION: (1)..(39)

<400> SEQUENCE: 13 accccctgccg gttctgtttt ctccaccgag tactgggcc        39

<210> SEQ ID NO 14

-continued

```
<211> LENGTH: 39
<212> TYPE: DNA
<213> ORGANISM: Artificial Sequence
<220> FEATURE:
<223> OTHER INFORMATION: primer_S429V
<220> FEATURE:
<221> NAME/KEY: DNA
<222> LOCATION: (1)..(39)

<400> SEQUENCE: 14
gccggttctt ccttcgttac cgagtactgg gccctcctg                              39

<210> SEQ ID NO 15
<211> LENGTH: 36
<212> TYPE: DNA
<213> ORGANISM: Artificial Sequence
<220> FEATURE:
<223> OTHER INFORMATION: primer_F521W
<220> FEATURE:
<221> NAME/KEY: DNA
<222> LOCATION: (1)..(36)

<400> SEQUENCE: 15
gaactaccgc tccaactggc accccgtcgg caccac                                 36

<210> SEQ ID NO 16
<211> LENGTH: 39
<212> TYPE: DNA
<213> ORGANISM: Artificial Sequence
<220> FEATURE:
<223> OTHER INFORMATION: primer_F521Y
<220> FEATURE:
<221> NAME/KEY: DNA
<222> LOCATION: (1)..(39)

<400> SEQUENCE: 16
aactaccgct ccaactatca ccccgtcggc accaccgcc                              39

<210> SEQ ID NO 17
<211> LENGTH: 38
<212> TYPE: DNA
<213> ORGANISM: Artificial Sequence
<220> FEATURE:
<223> OTHER INFORMATION: primer_V567A
<220> FEATURE:
<221> NAME/KEY: DNA
<222> LOCATION: (1)..(38)

<400> SEQUENCE: 17
tttgcggcca ccttgcctcc actctctacg ccattgcc                               38

<210> SEQ ID NO 18
<211> LENGTH: 39
<212> TYPE: DNA
<213> ORGANISM: Artificial Sequence
<220> FEATURE:
<223> OTHER INFORMATION: primer_V567G
<220> FEATURE:
<221> NAME/KEY: DNA
<222> LOCATION: (1)..(39)

<400> SEQUENCE: 18
gtttgcggcc accttgggtc cactctctac gccattgcc                              39

<210> SEQ ID NO 19
<211> LENGTH: 39
<212> TYPE: DNA
<213> ORGANISM: Artificial Sequence
<220> FEATURE:
```

<210> SEQ ID NO 19
<211> LENGTH: 39
<212> TYPE: DNA
<213> ORGANISM: Artificial Sequence
<220> FEATURE:
<223> OTHER INFORMATION: primer_V567M
<220> FEATURE:
<221> NAME/KEY: DNA
<222> LOCATION: (1)..(39)

<400> SEQUENCE: 19
gtttgcggcc accttatgtc cactctctac gccattgcc         39

<210> SEQ ID NO 20
<211> LENGTH: 39
<212> TYPE: DNA
<213> ORGANISM: Artificial Sequence
<220> FEATURE:
<223> OTHER INFORMATION: primer_V567Q
<220> FEATURE:
<221> NAME/KEY: DNA
<222> LOCATION: (1)..(39)

<400> SEQUENCE: 20
gtttgcggcc accttcagtc cactctctac gccattgcc         39

<210> SEQ ID NO 21
<211> LENGTH: 39
<212> TYPE: DNA
<213> ORGANISM: Artificial Sequence
<220> FEATURE:
<223> OTHER INFORMATION: primer_V567S
<220> FEATURE:
<221> NAME/KEY: DNA
<222> LOCATION: (1)..(39)

<400> SEQUENCE: 21
gtttgcggcc accttagctc cactctctac gccattgcc         39

<210> SEQ ID NO 22
<211> LENGTH: 39
<212> TYPE: DNA
<213> ORGANISM: Artificial Sequence
<220> FEATURE:
<223> OTHER INFORMATION: primer_V567T
<220> FEATURE:
<221> NAME/KEY: DNA
<222> LOCATION: (1)..(39)

<400> SEQUENCE: 22
gtttgcggcc accttacgtc cactctctac gccattgcc         39

<210> SEQ ID NO 23
<211> LENGTH: 39
<212> TYPE: DNA
<213> ORGANISM: Artificial Sequence
<220> FEATURE:
<223> OTHER INFORMATION: primer_V567C
<220> FEATURE:
<221> NAME/KEY: DNA
<222> LOCATION: (1)..(39)

<400> SEQUENCE: 23
gtttgcggcc accttttgttc cactctctac gccattgcc         39

<210> SEQ ID NO 24
<211> LENGTH: 585
<212> TYPE: PRT
<213> ORGANISM: Colletotrichum gloeosporioides
<220> FEATURE:
<221> NAME/KEY: PRT
<222>

```
Met Leu Arg Ser Ile Val Ser Leu Pro Leu Ala Ala Thr Ala Leu
1               5                   10                  15

Ala Tyr Pro Ala Ala Ser Ser Gln Arg Phe Asp Tyr Val Ile Ile Gly
            20                  25                  30

Gly Gly Thr Ser Gly Leu Val Val Ala Asn Arg Leu Ser Glu Leu Lys
            35                  40                  45

Asn Val Thr Val Ala Val Ile Glu Ala Gly Asp Ser Val Tyr Asp Asn
        50                  55                  60

Val Asn Val Thr Ser Pro Ser Gly Tyr Gly Leu Ala Phe Gly Thr Asp
65                  70                  75                  80

Ile Asp Tyr Ala Tyr Gln Thr Ala Gln Lys Tyr Gly Gly Asn Lys
                85                  90                  95

Thr Gln Thr Leu Arg Ala Gly Lys Ala Leu Gly Gly Thr Ser Thr Ile
                100                 105                 110

Asn Gly Met Ala Tyr Thr Arg Ala Gln Asp Val Gln Ile Asp Ile Trp
            115                 120                 125

Glu Arg Leu Gly Asn Asp Gly Trp Asn Trp Asn Asn Leu Leu Lys Tyr
    130                 135                 140

Tyr Lys Lys Ser Glu Thr Leu Gln Ala Pro Thr Thr Val Gln Val Asp
145                 150                 155                 160

Asp Gly Val Thr Tyr Ile Pro Glu Gln His Gly Thr Ser Gly Pro Leu
                165                 170                 175

Lys Val Gly Trp Lys Ser Gly Gly Val Glu Lys Ser Phe Val Asp Val
            180                 185                 190

Leu Asn Gln Thr Tyr Asn Ala Val Gly Val Pro Ala Leu Lys Asp Ile
                195                 200                 205

Ala Gly Gly Asp Met Val Gly Trp Asn Ile Tyr Pro Ala Thr Leu Asp
    210                 215                 220

Thr Ala Leu Gln Val Arg Asp Asp Ala Ala Arg Ala Tyr Tyr Phe Pro
225                 230                 235                 240

Tyr Gln Asn Arg Thr Asn Phe Arg Val Phe Leu Asn Thr Glu Ala Gln
                245                 250                 255

Lys Leu Val Trp Ala Glu Gly Ala Glu Ala Thr Ala Ser Gly Val Leu
            260                 265                 270

Val Lys Asp Lys Thr Gly Ala Thr His Thr Val Tyr Ala Asn Lys Glu
275                 280                 285

Ile Ile Leu Ser Ala Gly Ser Leu Arg Ser Pro Leu Leu Leu Glu Gln
    290                 295                 300

Ser Gly Val Gly Asn Pro Glu Ile Leu Lys Ala Ala Gly Ile Gln Thr
305                 310                 315                 320

Lys Val Asn Leu Pro Thr Val Gly Glu Asn Leu Gln Asp Gln Met Asn
                325                 330                 335

Asn Gly Leu Ala Gln Thr Ser Ser Lys Asn Phe Thr Gly Val Thr Thr
            340                 345                 350

Phe Val Ala Tyr Pro Asn Val Asp Asp Val Phe Ala Asn Gln Thr Ala
            355                 360                 365

Ser Leu Ala Ala Asn Ile Lys Thr Gln Leu Ser Gln Trp Ala Ala Gln
    370                 375                 380

Val Ser Glu Tyr Thr Asn Gly Val Val Thr Lys Glu Gln Leu Asp Lys
385                 390                 395                 400

Phe Phe Asp Ile Gln Tyr Asp Leu Ile Phe Thr Asp Lys Val Pro Leu
                405                 410                 415
```

```
Ala Glu Ile Leu Ile Thr Pro Ala Gly Ser Ser Phe Ser Thr Glu Tyr
            420                 425                 430

Trp Ala Leu Leu Pro Phe Ala Arg Gly Asn Ile His Val Thr Gly Ala
            435                 440                 445

Asn Ser Ser Ala Ala Lys Ile Asn Pro Asn Tyr Phe Met Met Asp Trp
450                 455                 460

Asp Met Thr Glu Gln Ile Gly Thr Ala Lys Phe Ile Arg Gln Leu Tyr
465                 470                 475                 480

Lys Thr Ala Pro Leu Ser Gln Tyr Phe Ala Ser Glu Thr Lys Pro Gly
            485                 490                 495

Leu Ala Thr Ile Ala Glu Asp Ala Ser Asp Val Trp Ser Lys Trp
            500                 505                 510

Ile Leu Glu Asn Tyr Arg Ser Asn Phe His Pro Val Gly Thr Thr Ala
            515                 520                 525

Met Met Ser Lys Glu Leu Gly Gly Val Val Asp Ala Asn Leu Lys Val
            530                 535                 540

Tyr Gly Thr Ser Asn Val Arg Val Val Asp Ala Gly Val Leu Pro Phe
545                 550                 555                 560

Gln Val Cys Gly His Leu Val Ser Thr Leu Tyr Ala Ile Ala Glu Lys
            565                 570                 575

Ala Ser Asp Ile Ile Lys Ala Ser Ala
            580                 585

<210> SEQ ID NO 25
<211> LENGTH: 585
<212> TYPE: PRT
<213> ORGANISM: Colletotrichum gloeosporioides
<220> FEATURE:
<221> NAME/KEY: PRT
<222> LOCATION: (1)..(585)

<400> SEQUENCE: 25

Met Leu Arg Ser Ile Val Ser Leu Pro Leu Leu Ala Ala Thr Ala Leu
1               5                   10                  15

Ala Tyr Pro Ala Ala Ser Ser Gln Arg Phe Asp Tyr Val Ile Ile Gly
            20                  25                  30

Gly Gly Thr Ser Gly Leu Val Val Ala Asn Arg Leu Ser Glu Leu Lys
        35                  40                  45

Asn Val Thr Val Ala Val Ile Glu Ala Gly Asp Ser Val Tyr Asp Asn
50                  55                  60

Val Asn Val Thr Ser Pro Ser Gly Tyr Gly Leu Ala Phe Gly Thr Asp
65                  70                  75                  80

Ile Asp Tyr Ala Tyr Gln Thr Thr Ala Gln Lys Tyr Gly Gly Asn Lys
            85                  90                  95

Thr Gln Thr Leu Arg Ala Gly Lys Ala Leu Gly Gly Thr Ser Thr Ile
            100                 105                 110

Asn Gly Met Ala Tyr Thr Arg Ala Gln Asp Val Gln Ile Asp Ile Trp
            115                 120                 125

Glu Arg Leu Gly Asn Asp Gly Trp Asn Trp Asn Asn Leu Leu Lys Tyr
        130                 135                 140

Tyr Lys Lys Ser Glu Thr Leu Gln Pro Thr Thr Val Gln Ala Asp
145                 150                 155                 160

Asp Gly Val Thr Tyr Ile Pro Glu Gln His Gly Thr Ser Gly Pro Leu
            165                 170                 175

Lys Val Gly Trp Lys Ser Gly Gly Val Glu Lys Ser Phe Val Asp Val
            180                 185                 190
```

-continued

```
Leu Asn Gln Thr Tyr Asn Ala Val Gly Val Pro Ala Leu Lys Asp Ile
            195                 200                 205
Ala Gly Asp Met Val Gly Trp Asn Ile Tyr Pro Ala Thr Leu Asp
210                 215                 220
Thr Ala Leu Gln Val Arg Asp Asp Ala Arg Ala Tyr Tyr Phe Pro
225                 230                 235                 240
Tyr Gln Asn Arg Thr Asn Phe Arg Val Phe Leu Asn Thr Glu Ala Gln
                245                 250                 255
Lys Leu Val Trp Ala Glu Gly Ala Glu Ala Thr Ala Ser Gly Val Leu
            260                 265                 270
Val Lys Asp Lys Ser Gly Ala Thr His Thr Val Tyr Ala Asn Lys Glu
            275                 280                 285
Val Ile Leu Ser Ala Gly Ser Leu Arg Ser Pro Leu Leu Glu Gln
            290                 295                 300
Ser Gly Val Gly Asn Pro Glu Ile Leu Lys Ala Ala Gly Ile Gln Thr
305                 310                 315                 320
Lys Val Asn Leu Pro Thr Val Gly Glu Asn Leu Gln Asp Gln Met Asn
                325                 330                 335
Asn Gly Leu Ala Gln Thr Ser Ser Lys Asn Phe Thr Gly Val Thr Thr
            340                 345                 350
Phe Val Ala Tyr Pro Asn Val Asp Asp Val Phe Ala Asn Gln Thr Ala
            355                 360                 365
Ser Leu Ala Ala Asn Ile Lys Thr Gln Leu Ser Gln Trp Ala Ala Gln
370                 375                 380
Val Ser Glu Tyr Thr Asn Gly Val Val Thr Lys Glu Gln Leu Asp Arg
385                 390                 395                 400
Phe Phe Asp Ile Gln Tyr Asp Leu Ile Phe Thr Asp Lys Val Pro Leu
                405                 410                 415
Ala Glu Ile Leu Ile Thr Pro Ala Gly Ser Ser Phe Ser Thr Glu Tyr
            420                 425                 430
Trp Ala Leu Leu Pro Phe Ala Arg Gly Asn Ile His Val Thr Gly Ala
            435                 440                 445
Asn Ser Ser Thr Ala Lys Ile Asn Pro Asn Tyr Phe Met Met Asp Trp
450                 455                 460
Asp Met Thr Glu Gln Ile Gly Thr Ala Lys Phe Ile Arg Gln Leu Tyr
465                 470                 475                 480
Lys Thr Ala Pro Leu Ser Gln Tyr Phe Ala Ser Glu Thr Lys Pro Gly
                485                 490                 495
Leu Ala Thr Ile Ala Glu Asp Ala Ser Asp Val Trp Ser Lys Trp
            500                 505                 510
Ile Leu Glu Asn Tyr Arg Ser Asn Phe His Pro Val Gly Thr Ala
            515                 520                 525
Met Met Ser Glu Glu Leu Gly Gly Val Val Asp Ala Asn Leu Lys Val
530                 535                 540
Tyr Gly Thr Ser Asn Val Arg Val Asp Ala Gly Val Leu Pro Phe
545                 550                 555                 560
Gln Val Cys Gly His Leu Val Ser Thr Leu Tyr Ala Ile Ala Glu Lys
                565                 570                 575
Ala Ser Asp Ile Ile Lys Ala Ser Ala
            580                 585

<210> SEQ ID NO 26
<211> LENGTH: 587
```

```
<212> TYPE: PRT
<213> ORGANISM: Colletotrichum chlorophyti
<220> FEATURE:
<221> NAME/KEY: PRT
<222> LOCATION: (1)..(587)

<400> SEQUENCE: 26
```

Met Arg Ser Phe Leu Leu Ser Leu Pro Leu Phe Ala Ala Thr Ala Leu
1               5                   10                  15

Ala Tyr Pro Ala Ala Ser Ala Gln Arg Phe Asp Tyr Val Val Ile Gly
            20                  25                  30

Gly Gly Thr Ser Gly Leu Val Val Ala Asn Arg Leu Ser Glu Leu Lys
        35                  40                  45

Asn Val Thr Val Ala Val Ile Glu Ala Gly Asp Ser Val Phe Asn Asn
    50                  55                  60

Ala Asn Val Thr Asp Leu Gly Gly Tyr Gly Lys Ala Phe Gly Ser Ser
65                  70                  75                  80

Ile Asp Tyr Ala Phe Glu Thr Val Gly Gln Lys Tyr Gly Gly Asn Lys
                85                  90                  95

Thr Gln Thr Leu Arg Ala Gly Lys Ala Leu Gly Gly Thr Ser Thr Ile
            100                 105                 110

Asn Gly Met Ala Tyr Thr Arg Ala Gln Asp Val Gln Ile Asp Ile Trp
        115                 120                 125

Glu Arg Leu Gly Asn Asp Gly Trp Asn Trp Glu Asn Leu Leu Glu Tyr
    130                 135                 140

Tyr Lys Lys Ala Glu Thr Leu Gln Pro Pro Thr Thr Glu Gln Val Ala
145                 150                 155                 160

Asp Gly Val Thr Phe Thr Pro Glu Tyr His Gly Ser Asn Gly Pro Leu
                165                 170                 175

Lys Val Gly Trp Lys Pro Gly Met Val Asn Ser Ser Phe Val Asp Val
            180                 185                 190

Leu Asn Gln Thr Tyr Gly Ala Val Gly Val Pro Ala Leu Gln Asp Ile
        195                 200                 205

Ala Gly Gly Asp Met Val Gly Trp Asn Ile Tyr Pro Ala Thr Val Asp
    210                 215                 220

Thr Ala Leu Gln Val Arg Glu Asp Ala Ala Arg Ala Tyr Tyr Phe Pro
225                 230                 235                 240

Tyr Gln Asn Arg Thr Asn Leu Arg Val Phe Leu Asn Thr Glu Ala Gln
                245                 250                 255

Lys Leu Val Trp Ala Asn Ser Thr Glu Ala Thr Ala Ser Gly Val Leu
            260                 265                 270

Val Lys Asp Ser Thr Gly Ala Ser Arg Thr Ile Tyr Ala Asn Lys Glu
        275                 280                 285

Val Ile Ile Ser Ala Gly Ser Leu Arg Ser Pro Leu Leu Leu Glu Gln
    290                 295                 300

Ser Gly Val Gly Asn Pro Ser Ile Leu Met Ala Ala Gly Ile Gln Thr
305                 310                 315                 320

Lys Val Asn Leu Pro Thr Val Gly Glu Asn Leu Gln Asp Gln Met Asn
                325                 330                 335

Asn Gly Leu Ala Gln Ser Ser Lys Ala Phe Thr Gly Ser Thr Thr
            340                 345                 350

Phe Val Ala Tyr Pro Asn Val Asp Asp Val Phe Ala Glu Gln Ser Ala
        355                 360                 365

Ala Leu Ala Asp Asp Ile Lys Gly Arg Leu Ser Gln Trp Ala Ala Gln
    370                 375                 380

```
Val Ser Glu Tyr Thr Asn Gly Val Val Thr Lys Glu Gln Leu Asp Lys
385                 390                 395                 400

Phe Phe Asp Ile Gln Tyr Asp Leu Ile Phe Thr Asp Lys Val Pro Leu
            405                 410                 415

Ala Glu Ile Leu Ile Thr Pro Ala Gly Ser Ser Phe Ser Thr Glu Tyr
        420                 425                 430

Trp Ala Leu Leu Pro Phe Ala Arg Gly Asn Ile His Val Gly Gly Ala
            435                 440                 445

Asn Ser Ser Ser Pro Lys Ile Asn Pro Asn Tyr Phe Met Met Asp Trp
450                 455                 460

Asp Met Thr Glu Gln Ile Gly Thr Ala Lys Phe Ile Arg Gln Leu Tyr
465                 470                 475                 480

Lys Thr Ala Pro Leu Ser Glu Tyr Phe Ala Asn Glu Thr Lys Pro Gly
                485                 490                 495

Leu Asn Val Ile Pro Glu Asp Ala Ser Asp Val Trp Ser Lys Trp
            500                 505                 510

Val Ile Glu Asn Tyr Arg Ser Asn Phe His Pro Val Gly Thr Thr Ala
        515                 520                 525

Met Met Ser Arg Glu Leu Gly Gly Val Val Asp Ala Asn Leu Lys Val
530                 535                 540

Tyr Gly Thr Thr Asn Val Arg Val Val Asp Ala Gly Ile Leu Pro Phe
545                 550                 555                 560

Gln Val Cys Gly His Leu Val Ser Thr Leu Tyr Ala Ile Ala Glu Lys
                565                 570                 575

Ala Ser Asp Ile Ile Lys Ala Ser Ala Trp Glu
            580                 585

<210> SEQ ID NO 27
<211> LENGTH: 588
<212> TYPE: PRT
<213> ORGANISM: Colletotrichum orbiculare
<220> FEATURE:
<221> NAME/KEY: PRT
<222> LOCATION: (1)..(588)

<400> SEQUENCE: 27

Met Met Arg Ser Leu Ile Ser Leu Pro Leu Phe Ala Ala Ala Leu
1               5                   10                  15

Ser Tyr Pro Thr Ala Ser Asn Asp Arg Phe Asp Tyr Val Ile Val Gly
            20                  25                  30

Gly Gly Thr Ser Gly Leu Val Val Ala Asn Arg Leu Ser Glu Leu Lys
        35                  40                  45

Asn Val Thr Val Ala Val Ile Glu Ala Gly Gly Ser Val Tyr Asp Asn
50                  55                  60

Ala Asn Val Thr Asp Leu Gly Gly Tyr Gly Lys Ala Phe Asp Thr Ser
65                  70                  75                  80

Ile Asp Tyr Ala Tyr Glu Thr Val Gly Gln Lys Tyr Gly Gly Asn Lys
                85                  90                  95

Thr Gln Thr Leu Arg Ala Gly Lys Ala Leu Gly Gly Thr Ser Thr Ile
            100                 105                 110

Asn Gly Met Ala Tyr Thr Arg Ala Gln Ser Ala Gln Val Asp Ile Trp
        115                 120                 125

Glu Lys Leu Gly Asn Asp Gly Trp Asn Trp Asp Asn Leu Leu Glu Tyr
130                 135                 140

Tyr Lys Lys Ser Glu Thr Leu Glu Arg Pro Thr Ala Glu Gln Ala Ala
```

-continued

```
            145                 150                 155                 160
His Gly Ala Thr Phe Ile Pro Glu Gln His Gly Thr Ser Gly Pro Leu
                165                 170                 175
Lys Val Gly Trp Lys Pro Asn Met Val Glu His Ser Phe Val Asp Val
                180                 185                 190
Leu Asn Gln Thr Tyr Ser Ser Val Gly Val Pro Ala Leu Gln Asp Ile
                195                 200                 205
Ala Gly Gly Asp Met Val Gly Trp Asn Ile Tyr Pro Ala Thr Val Asp
    210                 215                 220
Thr Thr Leu Gln Val Arg Glu Asp Ala Ala Arg Ala Tyr Tyr Phe Pro
225                 230                 235                 240
Tyr Gln Asn Arg Thr Asn Ile Arg Val Phe Leu Tyr Thr Glu Ala Gln
                245                 250                 255
Lys Leu Val Trp Ser Asn Ser Ser Thr Ala Asp Ala Thr Ala Ser
                260                 265                 270
Gly Val Leu Val Lys Asp Ala Thr Gly Ala Val Arg Thr Ile His Ala
                275                 280                 285
Asn Lys Glu Val Ile Leu Ser Ala Gly Ser Leu Arg Ser Pro Leu Leu
    290                 295                 300
Leu Glu Gln Ser Gly Val Gly Asn Pro Ser Ile Leu Lys Ala Ala Gly
305                 310                 315                 320
Ile Asp Pro Lys Val Val Leu Pro Thr Val Gly Glu Asn Leu Gln Asp
                325                 330                 335
Gln Met Asn Asn Gly Leu Ala Gln Thr Ser Thr Lys Asn Phe Thr Gly
                340                 345                 350
Ala Thr Thr Phe Val Ala Tyr Pro Asn Val Asp Asp Val Phe Ala Asp
                355                 360                 365
Arg Thr Ala Ala Leu Ala Ala Asp Val Lys Arg Lys Leu Pro Arg Trp
    370                 375                 380
Ala Arg Gln Thr Ser Glu Arg Thr Asn Gly Ala Val Thr Thr Arg Gln
385                 390                 395                 400
Leu Ala Ala Phe Phe Asp Met Gln Tyr Asp Leu Ile Phe Thr Ser Lys
                405                 410                 415
Val Pro Leu Ala Glu Ile Leu Val Thr Pro Ala Ala Gly Ala Phe Ser
                420                 425                 430
Thr Glu Tyr Trp Ala Leu Leu Pro Phe Ala Arg Gly Asn Ile His Val
                435                 440                 445
Arg Arg Ala Gly Ser Ser Ala Ala Arg Ile Asp Pro Asn Tyr Phe Met
    450                 455                 460
Met Asp Trp Asp Met Thr Glu Gln Val Gly Thr Ala Lys Phe Ile Arg
465                 470                 475                 480
Arg Leu Tyr Asp Thr Ala Pro Leu Ser Glu Tyr Phe Ala Gly Glu Thr
                485                 490                 495
Lys Pro Gly Leu Asp Val Val Ala Glu Asp Ala Glu Asp Val Trp
                500                 505                 510
Ser Arg Trp Ile Thr Glu Asn Tyr Arg Ser Asn Phe His Pro Val Gly
    515                 520                 525
Thr Thr Ala Met Met Ser Arg Glu Leu Gly Gly Val Val Asp Ala Asn
                530                 535                 540
Leu Lys Val Tyr Gly Thr Ser Asn Val Arg Val Val Asp Ala Gly Ile
545                 550                 555                 560
Leu Pro Phe Gln Val Cys Gly His Leu Val Ser Thr Leu Tyr Ala Val
                565                 570                 575
```

```
Ala Glu Lys Ala Ser Asp Ile Ile Lys Ala Ser Ala
            580                 585
```

<210> SEQ ID NO 28
<211> LENGTH: 581
<212> TYPE: PRT
<213> ORGANISM: Botryosphaeria parva
<220> FEATURE:
<221> NAME/KEY: PRT
<222> LOCATION: (1)..(581)

<400> SEQUENCE: 28

```
Met Tyr Arg Val Leu Ala Thr Ala Pro Leu Ala Ala Thr Ala Leu
1               5                   10                  15

Ala Ala Pro Ala Ala Pro Ala Lys Tyr Asp Tyr Ile Val Val Gly Gly
            20                  25                  30

Gly Thr Ser Gly Leu Val Val Ala Asn Arg Leu Ser Glu Leu Asn Asn
            35                  40                  45

Val Thr Val Ala Val Ile Glu Ala Gly Gly Ser Val Phe Thr Asn Glu
    50                  55                  60

Asn Val Thr Asn Pro Asn Gly Tyr Gly Leu Ala Phe Gly Thr Pro Ile
65              70                  75                  80

Asp Trp Ala Tyr Glu Ser Val Asn Gln Thr Tyr Gly Gly Lys Thr
                85                  90                  95

Gln Thr Leu Arg Ala Gly Lys Ala Leu Gly Gly Thr Ser Thr Ile Asn
            100                 105                 110

Gly Met Ala Tyr Thr Arg Ala Glu Asp Ala Gln Val Asp Ala Trp Glu
            115                 120                 125

Ala Ile Gly Asn Thr Gly Trp Asn Trp Ala Ser Leu Leu Pro Tyr Tyr
        130                 135                 140

Lys Lys Ser Glu Arg Val Gln Pro Pro Lys Ala Asp Gln Leu Ala Gly
145                 150                 155                 160

Gly Ala Thr Tyr Asp Pro Ala Phe His Gly Thr Ser Gly Pro Leu Lys
                165                 170                 175

Val Gly Trp Lys Asn Gly Met Met Asn Ile Ser Phe Pro Glu Asp Leu
            180                 185                 190

Asn Gln Thr Tyr Ala Ala Asn Gly Val Pro Tyr Ile Tyr Asp Ile Ala
        195                 200                 205

Gly Gly Lys Met Ala Gly Trp Asn Val Phe Pro Ser Thr Leu Asp Val
    210                 215                 220

Asp Leu Asn Val Arg Glu Asp Ala Ala Arg Ala Tyr Tyr Phe Pro Phe
225                 230                 235                 240

Glu Asn Arg Thr Asn Tyr His Val Leu Leu Asn Thr Glu Ala Gln Lys
                245                 250                 255

Leu Val Trp Ala Glu Ser Gly Ala Glu Ala Thr Ala Ser Gly Val Leu
            260                 265                 270

Val Lys Asp Ala Ser Gly Asn Thr Arg Thr Ile Tyr Ala Asn Lys Glu
        275                 280                 285

Val Ile Leu Ser Ala Gly Ser Leu Lys Ser Pro Val Leu Leu Glu Leu
    290                 295                 300

Ser Gly Val Gly Asn Ala Asp Ile Leu Lys Ala Gly Val Glu Val
305                 310                 315                 320

Lys Val Asp Leu Pro Ala Val Gly Glu Asn Leu Gln Asp Gln Thr Asn
                325                 330                 335

Asn Gly Phe Lys Gly Val Ala Thr Lys Ala Phe Thr Gly Asn Ala Val
```

-continued

```
                    340                 345                 350
Asn Val Ala Tyr Pro Asn Val Glu Asp Ile Phe Gly Asn Lys Thr Leu
            355                 360                 365

Thr Val Ala Ala Asp Val Lys Lys Ser Leu Gln Lys Tyr Ala Glu Glu
    370                 375                 380

Ala Ser Ala Tyr Ser Asn Gly Val Val Ala Val Asp Ser Leu Thr Lys
385                 390                 395                 400

Phe Phe Asp Ile Gln Tyr Asp Leu Ile Phe Lys Asp Lys Val Pro Leu
                405                 410                 415

Ala Glu Val Leu Ile Tyr Pro Thr Asp Thr Ala Phe Ser Ala Glu Phe
            420                 425                 430

Trp Ser Leu Leu Pro Phe Ala Arg Gly Asn Val His Ile Ala Ser Ala
            435                 440                 445

Asp Ala Ala Ser Ala Lys Ile Asn Pro Asn Tyr Tyr Met Phe Asp Trp
    450                 455                 460

Asp Met Thr Glu Gln Ile Gly Thr Ala Lys Tyr Ile Arg Gln Leu Phe
465                 470                 475                 480

Gly Thr Ala Pro Leu Ser Thr Leu Leu Ala Asn Glu Thr Ser Pro Gly
                485                 490                 495

Ala Ala Val Ala Ser Asp Ala Gln Phe Glu Ser Trp Ile Leu Glu Asn
            500                 505                 510

Tyr Arg Ser Asn Phe His Pro Val Gly Thr Thr Ala Met Met Pro Lys
            515                 520                 525

Glu Leu Gly Gly Val Val Asp Pro Ser Leu Lys Val Tyr Gly Thr Ser
    530                 535                 540

Asn Val Arg Val Val Asp Ala Gly Val Leu Pro Phe Gln Val Cys Gly
545                 550                 555                 560

His Leu Val Ser Thr Leu Tyr Ala Val Ala Glu Lys Ala Ser Asp Ile
                565                 570                 575

Ile Lys Ala Glu Ala
                580
```